United States Patent
Starr et al.

(10) Patent No.: US 8,795,627 B2
(45) Date of Patent: Aug. 5, 2014

(54) TREATMENT OF LIVER DISORDERS BY ADMINISTRATION OF RAP CONJUGATES

(75) Inventors: Christopher M. Starr, Sonoma, CA (US); Todd C. Zankel, San Francisco, CA (US)

(73) Assignee: Raptor Pharmaceuticals Inc., Novato, CA (US)

( * ) Notice: Subject to any disclaimer, the term of this patent is extended or adjusted under 35 U.S.C. 154(b) by 842 days.

(21) Appl. No.: 12/441,618

(22) PCT Filed: Sep. 18, 2007

(86) PCT No.: PCT/US2007/078792
§ 371 (c)(1),
(2), (4) Date: Oct. 29, 2009

(87) PCT Pub. No.: WO2008/036682
PCT Pub. Date: Mar. 27, 2008

(65) Prior Publication Data
US 2012/0251444 A1     Oct. 4, 2012

Related U.S. Application Data

(60) Provisional application No. 60/919,295, filed on Mar. 21, 2007.

(51) Int. Cl.
C07K 14/705 (2006.01)
A61K 38/17 (2006.01)
A61K 47/48 (2006.01)

(52) U.S. Cl.
CPC .................. *A61K 38/17* (2013.01); *A61K 47/48* (2013.01); *C07K 14/705* (2013.01)
USPC ......................................... 424/1.69; 514/19.3

(58) Field of Classification Search
CPC .......... A61K 38/00; A61K 47/00; C07K 14/00
See application file for complete search history.

(56) References Cited

U.S. PATENT DOCUMENTS

| | | | |
|---|---|---|---|
| 4,391,904 | A | 7/1983 | Litman et al. |
| 4,394,448 | A | 7/1983 | Szoka, Jr. et al. |
| 5,186,941 | A | 2/1993 | Callahan et al. |
| 5,474,766 | A | 12/1995 | Schwartz et al. |
| 5,962,012 | A | 10/1999 | Lin et al. |
| 5,994,129 | A | 11/1999 | Armstrong et al. |
| 6,048,729 | A | 4/2000 | Selden et al. |
| 6,063,630 | A | 5/2000 | Treco et al. |
| 6,069,167 | A | 5/2000 | Sokol |
| 6,261,595 | B1 | 7/2001 | Stanley et al. |
| 6,447,775 | B1 | 9/2002 | Strickland et al. |
| 6,596,762 | B2 | 7/2003 | Sokol |
| 7,560,431 | B2 * | 7/2009 | Zankel et al. ............... 514/1.1 |
| 2006/0029586 | A1 | 2/2006 | Chen et al. |
| 2006/0029609 | A1 * | 2/2006 | Zankel et al. .............. 424/178.1 |

FOREIGN PATENT DOCUMENTS

| | | |
|---|---|---|
| JP | 08-253430 | 10/1996 |
| WO | WO-1995/025536 | 9/1995 |
| WO | WO-2000/24782 A2 | 5/2000 |
| WO | WO-2005/002515 | 1/2005 |
| WO | WO-2006/138343 | 12/2006 |

OTHER PUBLICATIONS

Prince et al., Lipoprotein receptor binding, cellular uptake, and lysosomal delivery of fusions between the receptor-associated protein (RAP) and alpha-L-iduronidase or acid alpha-gluconase, Aug. 23, 2004, J. Biol. Chem. 279(33):35037-35046.*
Verges et al. Endocytosis of hepatic lipase and lipoprotein lipase into rat liver hepatocytes in vivo is mediated by low density lipoprotein receptor-related protein, Mar. 5, 2004, J. Biol. Chem. 279(10):9030-9036.*
Anderson et al., Dominant Thermodynamic Role of the Third Independent Receptor Binding Site in the Receptor-Associated Protein RAP. *Biochemistry*, 40: 15408-17 (2001).
Anderson et al., Identification of the minimal functional unit in the low density lipoprotein receptor-related protein for binding the receptor-associated protein (RAP). *J. Biol. Chem.* 275: 21017-24 (2000).
Ashcom et al., The human α2-kD cell surface glycoprotein specific for the activated conformation of α2-macroglobulin. *J. Cell Biol.* 110: 1041-8 (1990).
Bogan et al., Anatomy of hot spots in protein interfaces. *J. Mol. Biol.* 280: 1-9 (1998).
Bu et al., Receptor-mediated endocytosis of tissue-type plasminogen activator by low density lipoprotein receptor-related protein on human hepatoma HepG2 cells. *J. Biol. Chem.* 268: 13002-9 (1993).
Bu et al., RAP, a novel type of ER chaperone. *Trends. Cell. Biol.* 8: 272-6 (1998).
Chan et al., Inhibition of P-glycoprotein expression and reversal of drug resistance of human hepatoma HepG2 cells by multidrug resistance gene (mdr1) antisense RNA.*Life. Sci.* 67: 2117-24 (2000).
Christensen et al., Megalin and cubilin: Synergistic endocytic receptors in renal proximal tubule. Am. J. Physiol. Renal Physiol. 280: F562-73 (2001).
Clackson et al., A hot spot of binding energy in a hormone-receptor interface. *Science*, 267: 383-6 (1995).
Danesi et al., Pharmacokinetic-pharmacodynamic relationships of the anthracycline anticancer drugs. *Clin. Pharmacokinet.* 41: 431-44 (2002).
Davidsen et al., The plasma clearance of human alpha 2-macroglobulin-trypsin complex in the rat is mainly accounted for by uptake into hepatocytes. Biochim. Biophys. Acta. 846: 85-92 (1985).
DeLano et al., Unraveling hot spots in binding interfaces: progress and challenges. *Curr Opin. Struct. Biol.* 12: 14-20 (2002).
Domingo et al., Multiple display of peptides and proteins on a macromolecular scaffold derived from a multienzyme complex. *J. Mol. Biol.* 305(2):259-67 (2001).

(Continued)

*Primary Examiner* — John Ulm
(74) *Attorney, Agent, or Firm* — Marshall, Gerstein & Borun LLP

(57) ABSTRACT

The present invention relates to the use of receptor-associate protein (RAP) and fragments and variants thereof to improve delivery of therapeutic compounds to the liver and provides methods to treat liver disorders and conditions, such as hepatic carcinoma, by administering RAP or RAP variants conjugated to active agents.

27 Claims, 5 Drawing Sheets

(56) References Cited

OTHER PUBLICATIONS

Dwyer et al., High Affinity RNase S-Peptide Variants Obtained by Phage Display Have a Novel "Hot-Spot" of Binding Energy. *Biochemistry*, 40: 13491-500 (2001).
El-Serag et al., Risk factors for the rising rates of primary liver cancer in the United States. *Arch. Intern. Med.* 160: 3227-30 (2000).
El-Serag et al., Trends in survival of patients with hepatocellular carcinoma between 1977 and 1996 in the United States. *Hepatology*, 33: 62-65 (2001).
El-Serag et al., Rising incidence of hepatocellular carcinoma in the United States. *N. Engl. J. Med.* 340: 745-50 (1999).
Farquhar et al., Functional domains of the receptor-associated protein (RAP). *Proc. Nat. Acad. Sci. USA.* 91: 3161-3162 (1994).
Fisher et al., Structure of an LDLR-RAP complex reveals a general mode for ligand recognition by lipoprotein receptors. *Mol. Cell*, 22: 277-83 (2006).
FitzGerald et al., Pseudomonas exotoxin-mediated selection yields cells with altered expression of low-density lipoprotein receptor-related protein. *J. Cell Biol.* 129(6): 1533-41 (1995).
Frederickson et al., A rationally designed agonist antibody fragment that functionally mimics thrombopoietin. *Proc. Natl. Acad. Sci. USA.* 103(39): 14307-12 (2006).
Funk et al., The role of hepatic transporters in drug elimination. *Exp. Opin. Drug Metab. Toxicol*, 4(4): 363-79 (2008).
Gao et al., Structure-based method for analyzing protein—protein interfaces. *J. Mol. Model (Online)*, 10: 44-54 (2004).
Gao et al., Nude mice model of human hepatocellular carcinoma via orthotopic implantation of histologically intact tissue. *World. J. Gastroenterol.* 10: 3107-3111 (2004).
Gish, Hepatocellular carcinoma: overcoming challenges in disease management. *Clin. Gastroenterol. Hepatol.* 4: 252-61 (2006).
Guillaume et al., Soluble major histocompatibility complex-peptide octamers with impaired CD8 binding selectively induce Fas-dependent apoptosis. *J. Biol. Chem.* 278(7): 4500-9 (2003).
Halperin et al., Protein-protein interactions: Coupling of structurally conserved residues and of hot spots across interfaces. Implications for docking. *Structure*, 12: 1027-38 (2004).
Herz et al., 39-kDa protein modulates binding of ligands to low density lipoprotein receptor-related protein/α2-macroglobulin receptor. *J. Biol. Chem.* 266: 21232-8 (1991).
Herz et al., Initial hepatic removal of chylomicron remnants is unaffected but endocytosis is delayed in mice lacking the low density lipoprotein receptor. Proc. Natl'. *Acad. Sci. USA.* 92: 4611-5 (1995).
Hollestelle et al., Factor VIII expression in liver disease. *Thromb. Haemost*, 91: 267-75 (2004).
Horn et al., Molecular analysis of ligand binding to the second cluster of complement-type repeats of the low density lipoprotein receptor-related protein. *J. Biol. Chem.* 272: 13608-13 (1997).
Hosse et al., A new generation of protein display scaffolds for molecular recognition. *Protein Sci.* 15:14-27 (2006).
Hu et al., Genetic alterations in doxorubicin-resistant hepatocellular carcinoma cells: a combined study of spectral karyotyping, positional expression profiling and candidate genes. *Int. J. Oncol.* 25: 1357-64 (2004).
Iadonato et al., Interaction of a 39 kDa protein with the low-density-lipoprotein-receptor-related protein (LRP) on rat hepatoma cells. *Biochem. J.* 296 (Pt 3): 867-75 (1993).
Jensen et al., Purification of the human placental alpha2-macroglobulin receptor. FEBS Lett. 255: 275-80 (1989).
Kim et al., Gene transfer into human hepatoma cells by receptor-associated protein/polylysine conjugates. *Bioconjug. Chem.*, 15: 326-32 (2004).
Laithwaite et al., Divergent Pseudomonas exotoxin A sensitivity in normal and transformed liver cells is correlated with low-density lipoprotein receptor-related protein expression. *Toxicon.* 39: 1283-1290 (2001).
Lau et al., Transarterial chemoembolization for hepatocellular carcinoma. *J. Am. Coll. Surg.* 202: 155-68 (2006).
Lazic, et al., Structural organization of the receptor associated protein. *Biochemistry.*, 42: 14913-20 (2003).
Li et al., Magnitude of the hydrophobic effect at central versus peripheral sites in protein-protein interfaces. *Structure*, 13: 297-307 (2005).
Li et al., Differential functions of members of the low density lipoprotein receptor family suggested by their distinct endocytosis rates. *J. Biol. Chem.* 276: 18000-6 (2001).
Lin et al., Local injection therapy for hepatocellular carcinoma. *Hepatobiliary. Pancreat. Dis. Int.* 5: 16-21 (2006).
Ludtke et al., Peptide-mediated targeting of hepatocytes via low density lipoprotein receptor-related protein (LRP) targeting hepatocytes via *LRP. Drug Deliv.*, 16(5): 268-73 (2009).
Mahley et al., Remnant lipoprotein metabolism: key pathways involving cell-surface heparan sulfate proteoglycans and apolipoprotein E. *J. Lipid. Res.* 40:1-16 (1999).
Marrero, Hepatocellular carcinoma. *Curr. Opin. Gastroenterol.* 22: 248-53 (2006).
Medved et al., Domain organization of the 39-kDa receptor-associated protein. *J. Biol. Chem.* 274(2): 717-27 (1999).
Meilinger et al., Removal of lactoferrin from plasma is mediated by binding to low density lipoprotein receptor-related protein/alpha2-macroglobulin receptor and transport to endosomes. *FEBS Lett.* 360: 70-4 (1995).
Melman et al., High affinity binding of receptor-associated protein to heparin and low density lipoprotein receptor-related protein requires similar basic amino acid sequence motifs. *J. Biol. Chem.* 276: 29338-46 (2001).
Migliorini et al., Allosteric modulation of ligand binding to low density lipoprotein receptor-related prptein by the receptor-associated protein required critical lysine residues within its carboxyl-terminal domain. *J. Biol. Chem.* 278: 17986-92 (2003).
Moestrup et al., Distribution of the alpha2-macroglubulin receptor/low density lipoprotein receptor-related protein in human tussues. *Cell Tissue Res.*, 269(3): 375-82 (1992).
Narita et al., Two receptor systems are involved in the plasma clearance of tissue factor pathway inhibitor in vivo. *J. Biol. Chem*, 270: 24800-4 (1995).
Neels et al., The second and fourth cluster of class A cysteine-rich repeats of the low density lipoprotein receptor-related protein share ligand-binding properties. *J. Biol. Chem.* 274: 3130511 (1999).
Nielsen et al., The solution structure of the N-terminal domain of alpha2-macroglobulin receptor-associated protein. *Proc. Natl. Acad. Sci. USA.* 94: 7521-5 (1997).
Obermoeller et al., Differential functions of triplicated repeats suggest two independent roles for the receptor-associated protein as a molecular chaperone. *J. Biol. Chem.* 272: 10761-8 (1997).
Orlando et al., Functional domains of the receptor-associated protein (RAP). *Proc. Natl. Acad. Sci. USA.* 3161-3 (1994).
Plosker et al., Epirubicin. A review of its pharmacodynamic and pharmacokinetic properties, and therapeutic use in cancer chemotherapy. *Drugs*, 45: 788-856 (1993).
Prince et al., Lipoprotein Receptor Binding, Cellular Uptake, and Lysosomal Delivery of Fusions between the Receptor-associated Protein (RAP) and α-l-Iduronidase or Acid α-Glucosidase. J. Biol. Chem. 279: 35037-46 (2004).
Rall et al., The domain structure of human receptor-associated protein. *J. Biol. Chem.* 273(37): 24152-7 (1998).
Ribero et al., Liver resection in the treatment of hepatocellular carcinoma. *Expert. Rev. Anticancer. Ther.* 6: 567-79 (2006).
Rosebrough et al., Biochemical modification of streptavidin and avidin: in vitro and in vivo analysis. *J. Nucl. Med.* 37: 1380-4 (1996).
Savonen et al., The carboxyl-terminal domain of receptor-associated protein facilitates protein folding and trafficking of the very low density lipoprotein receptor by interaction with the three amino-terminal ligand-binding repeats of the receptor. *J. Biol. Chem.* 274(36): 25877-82 (1999).
Strickland et al., Primary structure of [alpha]2-macroglobulin receptor-associated protein: Human homologue of a Heymann nephritis antigen. *J. Biol. Chem.*, 266(20): 13364-9 (1991).
Tennant et al., Hepatocellular carcinoma in the woodchuck model of hepatitis B virus infection. *Gastroenterology.* 127: S283-93 (2004).

(56) References Cited

OTHER PUBLICATIONS

Verges et al., Endocytosis of hepatic lipase and lipoprotein lipase into rat liver hepatocytes in vivo is mediated by the low density lipoprotein receptor-related protein. *J Biol. Chem.* 279: 9030-6 (2004).

Warshawsky et al., Binding analysis of amino-terminal and carboxyl-terminal regions of the 39-kDa protein to the low density lipoprotein receptor-related protein. *J. Biol. Chem.* 269: 3325-30 (1994).

Warshawsky et al., Identification of domains on the 39-kDa protein that inhibit the binding of ligands to the low density lipoprotein receptor-related protein. *J. Biol. Chem.* 268: 22046-54 (1993).

Warshawsky et al., 39-kD protein inhibits tissue-type plasminogen activator clearance in vivo. *J. Clin. Invest.* 92: 937-344 (1993).

Wilbur et al., Streptavidin in antibody pretargeting. Comparison of a recombinant streptavidin with two streptavidin mutant proteins and two commercially available streptavidin proteins. *Bioconjug. Chem.* 9: 100-7 (1998).

Williams et al., A novel mechanism for controlling the activity of alpha2-macroglobulin receptor/low density lipoprotein receptor-related protein. *J. Biol. Chem.* 267: 9035-40 (1992).

Willnow et al., Low density lipoprotein receptor-related protein and gp330 bind similar ligands, including plasminogen activator-inhibitor complexes and lactoferrin, an inhibitor of chylomicron remnant clearance. *J. Biol. Chem.* 267(36): 26172-80 (1992).

Wu et al., Targeting hepatocytes for drug and gene delivery: emerging novel approaches and applications. *Frontiers Biosci.,* 7: D717-25 (2002).

Yu et al., LDL receptor-related protein mediates cell-surface clustering and hepatic sequestration of chylomicron remnants in LDLR-deficient mice. *J. Clin. Invest.* 107: 1387-94 (2001).

Zhang et al., Multiple-peptide conjugates for binding beta-amyloid plaques of Alzheimer's disease. *Bioconjug. Chem.* 14: 86-92 (2003).

Zhou et al., Cholesteryl ester transfer protein (CETP) expression enhances HDL chlesteryl ester liver delivery, which is independent of scavenger receptor Bi, LDL receptor related protein and possibly LDL receptor. *Biochim. Biophys. Acta.,* 1761 (12): 1482-8 (2006).

Zhu, Systemic therapy of advanced hepatocellular carcinoma: how hopeful should we be? *Oncologist.* 11: 790-800 (2006).

International Search Report and Written Opinion of the International Searching Authority, United States Patent and Trademark Office, PCT/US2007/078792, dated May 27, 2008.

Supplementary European Search Report and Written Opinion issued in connection with European Application No. 07842713.5, dated Mar. 31, 2010.

\* cited by examiner

SEQUENCE LISTING

<160> NUMBER OF SEQ ID NOS: 15

<210> SEQ ID NO 1
<211> LENGTH: 323
<212> TYPE: PRT
<213> ORGANISM: Homo sapiens

<400> SEQUENCE: 1

Tyr Ser Arg Glu Lys Asn Gln Pro Lys Pro Ser Pro Lys Arg Glu Ser
1               5                   10                  15

Gly Glu Glu Phe Arg Met Glu Lys Leu Asn Gln Leu Trp Glu Lys Ala
            20                  25                  30

Gln Arg Leu His Leu Pro Pro Val Arg Leu Ala Glu Leu His Ala Asp
        35                  40                  45

Leu Lys Ile Gln Glu Arg Asp Glu Leu Ala Trp Lys Lys Leu Lys Leu
50                  55                  60

Asp Gly Leu Asp Glu Asp Gly Lys Glu Ala Arg Leu Ile Arg Asn
65                  70                  75                  80

Leu Asn Val Ile Leu Ala Lys Tyr Gly Leu Asp Gly Lys Lys Asp Ala
            85                  90                  95

Arg Gln Val Thr Ser Asn Ser Leu Ser Gly Thr Gln Glu Asp Gly Leu
        100                 105                 110

Asp Asp Pro Arg Leu Glu Lys Leu Trp His Lys Ala Lys Thr Ser Gly
    115                 120                 125

Lys Phe Ser Gly Glu Glu Leu Asp Lys Leu Trp Arg Glu Phe Leu His
130                 135                 140

His Lys Glu Lys Val His Glu Tyr Asn Val Leu Leu Glu Thr Leu Ser
145                 150                 155                 160

Arg Thr Glu Glu Ile His Glu Asn Val Ile Ser Pro Ser Asp Leu Ser
            165                 170                 175

Asp Ile Lys Gly Ser Val Leu His Ser Arg His Thr Glu Leu Lys Glu
        180                 185                 190

Lys Leu Arg Ser Ile Asn Gln Gly Leu Asp Arg Leu Arg Arg Val Ser
    195                 200                 205

His Gln Gly Tyr Ser Thr Glu Ala Glu Phe Glu Glu Pro Arg Val Ile
210                 215                 220

Asp Leu Trp Asp Leu Ala Gln Ser Ala Asn Leu Thr Asp Lys Glu Leu
225                 230                 235                 240

Glu Ala Phe Arg Glu Glu Leu Lys His Phe Glu Ala Lys Ile Glu Lys
            245                 250                 255

```
His Asn His Tyr Gln Lys Gln Leu Glu Ile Ala His Glu Lys Leu Arg
            260                 265                 270

His Ala Glu Ser Val Gly Asp Gly Glu Arg Val Ser Arg Ser Arg Glu
        275                 280                 285

Lys His Ala Leu Leu Glu Gly Arg Thr Lys Glu Leu Gly Tyr Thr Val
    290                 295                 300

Lys Lys His Leu Gln Asp Leu Ser Gly Arg Ile Ser Arg Ala Arg His
305                 310                 315                 320

Asn Glu Leu
```

<210> SEQ ID NO 2
<211> LENGTH: 123
<212> TYPE: PRT
<213> ORGANISM: Homo sapiens

<400> SEQUENCE: 2

```
Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Ala Gln Ser
            20                  25                  30

Ala Asn Leu Thr Asp Lys Glu Leu Glu Ala Phe Arg Glu Glu Leu Lys
        35                  40                  45

His Phe Glu Ala Lys Ile Glu Lys His Asn His Tyr Gln Lys Gln Leu
    50                  55                  60

Glu Ile Ala His Glu Lys Leu Arg His Ala Glu Ser Val Gly Asp Gly
65                  70                  75                  80

Glu Arg Val Ser Arg Ser Arg Glu Lys His Ala Leu Leu Glu Gly Arg
                85                  90                  95

Thr Lys Glu Leu Gly Tyr Thr Val Lys Lys His Leu Gln Asp Leu Ser
            100                 105                 110

Gly Arg Ile Ser Arg Ala Arg His Asn Glu Leu
        115                 120
```

<210> SEQ ID NO 3
<211> LENGTH: 71
<212> TYPE: PRT
<213> ORGANISM: Homo sapiens

<400> SEQUENCE: 3

```
Phe Arg Glu Glu Leu Lys His Phe Glu Ala Lys Ile Glu Lys His Asn
1               5                   10                  15

His Tyr Gln Lys Gln Leu Glu Ile Ala His Glu Lys Leu Arg His Ala
            20                  25                  30

Glu Ser Val Gly Asp Gly Glu Arg Val Ser Arg Ser Arg Glu Lys His
        35                  40                  45

Ala Leu Leu Glu Gly Arg Thr Lys Glu Leu Gly Tyr Thr Val Lys Lys
    50                  55                  60

His Leu Gln Asp Leu Ser Gly
65                  70
```

<210> SEQ ID NO 4
<211> LENGTH: 55
<212> TYPE: PRT
<213> ORGANISM: Homo sapiens

<400> SEQUENCE: 4

```
His Phe Glu Ala Lys Ile Glu Lys His Asn His Tyr Gln Lys Gln Leu
1               5                   10                  15
```

-continued

Glu Ile Ala His Glu Lys Leu Arg His Ala Glu Ser Val Gly Asp Gly
            20                  25                  30

Glu Arg Val Ser Arg Ser Arg Glu Lys His Ala Leu Leu Glu Gly Arg
        35                  40                  45

Thr Lys Glu Leu Gly Tyr Thr
    50                  55

<210> SEQ ID NO 5
<211> LENGTH: 119
<212> TYPE: PRT
<213> ORGANISM: Homo sapiens

<400> SEQUENCE: 5

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Ala Gln Ser
            20                  25                  30

Ala Asn Leu Thr Asp Lys Glu Leu Glu Ala Phe Arg Glu Glu Leu Lys
        35                  40                  45

His Phe Glu Ala Lys Ile Glu Lys His Asn His Tyr Gln Lys Gln Leu
    50                  55                  60

Glu Ile Ala His Glu Lys Leu Arg His Ala Glu Ser Val Gly Asp Gly
65                  70                  75                  80

Glu Arg Val Ser Arg Ser Arg Glu Lys His Ala Leu Leu Glu Gly Arg
                85                  90                  95

Thr Lys Glu Leu Gly Tyr Thr Val Lys Lys His Leu Gln Asp Leu Ser
            100                 105                 110

Gly Arg Ile Ser Arg Ala Arg
        115

<210> SEQ ID NO 6
<211> LENGTH: 1493
<212> TYPE: DNA
<213> ORGANISM: Homo sapiens

<400> SEQUENCE: 6
tgagcggggg atgatggcgc cgcggagggt caggtcgttt ctgcgcgggc tcccggcgct      60
gctactgctg ctgctcttcc tcgggccctg gcccgctgcg agccacggcg gcaagtactc     120
gcgggagaag aaccagccca gccgtccccg aaacgcgag tccggagagg agttccgcat      180
ggagaagttg aaccagctgt gggagaaggc ccagcgactg catcttcctc ccgtgaggct     240
ggccgagctc cacgctgatc tgaagataca ggagagggac gaactcgcct ggaagaaact     300
aaagcttgac ggcttggacg aagatgggga aaggaagcg agactcatac gcaacctcaa     360
tgtcatcttg gccaagtatg gtctggacgg aaagaaggac gctcggcagg tgaccagcaa     420
ctccctcagt ggcacccagg aagacgggct ggatgacccc aggctggaaa agctgtggca     480
caaggcgaag acctctggga aattctccgg cgaagaactg acaagctct ggcgggagtt      540 cctgcatcac aaagagaaag ttcacgagta acgtcctg ctggagaccc tgagcaggac       600
cgaagaaatc cacgagaacg tcattagccc ctcggacctg agcgacatca agggcagcgt     660
cctgcacagc aggcacacgg agctgaagga gaagctgcgc agcatcaacc agggcctgga     720
ccgcctgcgc agggtcagcc accagggcta cagcactgag gctgagttcg aggagcccag     780
ggtgattgac ctgtgggacc tggcgcagtc cgccaacctc acggacaagg agctggaggc     840
gttccgggag gagctcaagc acttcgaagc caaaatcgag aagcacaacc actaccagaa     900

```
gcagctggag attgcgcacg agaagctgag gcacgcagag agcgtgggcg acggcgagcg    960
tgtgagccgc agccgcgaga agcacgccct gctgggaggg cggaccaagg agctgggcta   1020
cacggtgaag aagcatctgc aggacctgtc cggcaggatc tccagagctc ggcacaacga   1080
actctgaagg cactggggag cccagcccgg cagggaagag gccagcgtga aggacctggg   1140
ctcttggccg tggcatttcc gtggacagcc cgccgtcagg gtggctgggg ctggcacggg   1200
tgtcgaggca ggaaggattg tttctggtga ctgcagccgc tgccgtcgcg acacagggct   1260
tggtggtggt agcatttggg tctgagatcg cccagctct gactgaaggg gcttggcttc    1320
cactcagcat cagcgtggca gtcaccaccc cagtgaggac ctcgatgtcc agctgctgtc   1380
aggtctgata gtcctctgct aaaacaacac gatttacata aaaaatctta cacatctgcc   1440
accggaaata ccatgcacag agtccttaaa aaatagagtg cagtatttaa acc           1493
```

<210> SEQ ID NO 7
<211> LENGTH: 357
<212> TYPE: PRT
<213> ORGANISM: Homo sapiens

<400> SEQUENCE: 7

```
Met Ala Pro Arg Arg Val Arg Ser Phe Leu Arg Gly Leu Pro Ala Leu
1               5                   10                  15

Leu Leu Leu Leu Phe Leu Gly Pro Trp Pro Ala Ala Ser His Gly
            20                  25                  30

Gly Lys Tyr Ser Arg Glu Lys Asn Gln Pro Lys Pro Ser Pro Lys Arg
        35                  40                  45

Glu Ser Gly Glu Glu Phe Arg Met Glu Lys Leu Asn Gln Leu Trp Glu
    50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
    130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
        195                 200                 205

Leu Ser Asp Ile Lys Gly Ser Val Leu His Ser Arg His Thr Glu Leu
    210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
                245                 250                 255

Val Ile Asp Leu Trp Asp Leu Ala Gln Ser Ala Asn Leu Thr Asp Lys
            260                 265                 270
```

```
Glu Leu Glu Ala Phe Arg Glu Leu Lys His Phe Glu Ala Lys Ile
        275                 280                 285

Glu Lys His Asn His Tyr Gln Lys Gln Leu Glu Ile Ala His Glu Lys
        290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
                340                 345                 350

Arg His Asn Glu Leu
                355

<210> SEQ ID NO 8
<211> LENGTH: 319
<212> TYPE: PRT
<213> ORGANISM: Homo sapiens

<400> SEQUENCE: 8

Tyr Ser Arg Glu Lys Asn Gln Pro Lys Pro Ser Pro Lys Arg Glu Ser
1               5                   10                  15

Gly Glu Glu Phe Arg Met Glu Lys Leu Asn Gln Leu Trp Glu Lys Ala
                20                  25                  30

Gln Arg Leu His Leu Pro Pro Val Arg Leu Ala Glu Leu His Ala Asp
            35                  40                  45

Leu Lys Ile Gln Glu Arg Asp Glu Leu Ala Trp Lys Lys Leu Lys Leu
        50                  55                  60

Asp Gly Leu Asp Glu Asp Gly Glu Lys Glu Ala Arg Leu Ile Arg Asn
65                  70                  75                  80

Leu Asn Val Ile Leu Ala Lys Tyr Gly Leu Asp Gly Lys Lys Asp Ala
                85                  90                  95

Arg Gln Val Thr Ser Asn Ser Leu Ser Gly Thr Gln Glu Asp Gly Leu
            100                 105                 110

Asp Asp Pro Arg Leu Glu Lys Leu Trp His Lys Ala Lys Thr Ser Gly
        115                 120                 125

Lys Phe Ser Gly Glu Glu Leu Asp Lys Leu Trp Arg Glu Phe Leu His
130                 135                 140

His Lys Glu Lys Val His Glu Tyr Asn Val Leu Leu Glu Thr Leu Ser
                145                 150                 155                 160

Arg Thr Glu Glu Ile His Glu Asn Val Ile Ser Pro Ser Asp Leu Ser
                165                 170                 175

Asp Ile Lys Gly Ser Val Leu His Ser Arg His Thr Glu Leu Lys Glu
            180                 185                 190

Lys Leu Arg Ser Ile Asn Gln Gly Leu Asp Arg Leu Arg Arg Val Ser
        195                 200                 205

His Gln Gly Tyr Ser Thr Glu Ala Glu Phe Glu Pro Arg Val Ile
    210                 215                 220

Asp Leu Trp Asp Leu Ala Gln Ser Ala Asn Leu Thr Asp Lys Glu Leu
225                 230                 235                 240

Glu Ala Phe Arg Glu Leu Lys His Phe Glu Ala Lys Ile Glu Lys
                245                 250                 255

His Asn His Tyr Gln Lys Gln Leu Glu Ile Ala His Glu Lys Leu Arg
            260                 265                 270

His Ala Glu Ser Val Gly Asp Gly Glu Arg Val Ser Arg Ser Arg Glu
```

```
            275                 280                 285
Lys His Ala Leu Leu Glu Gly Arg Thr Lys Glu Leu Gly Tyr Thr Val
    290                 295                 300

Lys Lys His Leu Gln Asp Leu Ser Gly Arg Ile Ser Arg Ala Arg
305                 310                 315

<210> SEQ ID NO 9
<211> LENGTH: 80
<212> TYPE: PRT
<213> ORGANISM: Artificial sequence
<220> FEATURE:
<223> OTHER INFORMATION: Synthetic peptide

<400> SEQUENCE: 9

Gly Gly Ser Gly Gly Cys Gly Phe Arg Glu Glu Leu Lys His Phe Glu
1               5                   10                  15

Ala Lys Ile Glu Lys His Asn His Tyr Gln Lys Gln Leu Glu Ile Ala
                20                  25                  30

His Glu Lys Leu Arg His Ala Glu Ser Val Gly Asp Gly Glu Arg Val
            35                  40                  45

Ser Arg Ser Arg Glu Lys His Ala Leu Leu Glu Gly Arg Thr Lys Glu
    50                  55                  60

Leu Gly Tyr Thr Val Lys Lys His Leu Gln Asp Leu Ser Gly Cys
65                  70                  75                  80

<210> SEQ ID NO 10
<211> LENGTH: 67
<212> TYPE: PRT
<213> ORGANISM: Artificial sequence
<220> FEATURE:
<223> OTHER INFORMATION: Synthetic peptide

<400> SEQUENCE: 10

Cys Gly Lys His Phe Glu Ala Lys Ile Glu Lys His Asn His Tyr Gln
1               5                   10                  15

Lys Gln Leu Glu Ile Ala His Glu Lys Leu Arg His Ala Glu Ser Val
                20                  25                  30

Gly Asp Gly Glu Arg Val Ser Arg Ser Arg Glu Lys His Ala Leu Leu
            35                  40                  45

Glu Gly Arg Thr Lys Glu Leu Gly Tyr Thr Val Lys Lys His Leu Gln
    50                  55                  60

Asp Gly Cys
65

<210> SEQ ID NO 11
<211> LENGTH: 60
<212> TYPE: PRT
<213> ORGANISM: Artificial sequence
<220> FEATURE:
<223> OTHER INFORMATION: Synthetic peptide

<400> SEQUENCE: 11

Cys Glu Ala Lys Ile Glu Lys His Asn His Tyr Gln Lys Gln Leu Glu
1               5                   10                  15

Ile Ala His Glu Lys Leu Arg His Ala Glu Ser Val Gly Asp Gly Glu
                20                  25                  30

Arg Val Ser Arg Ser Arg Glu Lys His Ala Leu Leu Glu Gly Arg Thr
            35                  40                  45

Lys Glu Leu Gly Tyr Thr Val Lys Lys His Gly Cys
    50                  55                  60
```

```
-continued

<210> SEQ ID NO 12
<211> LENGTH: 5
<212> TYPE: PRT
<213> ORGANISM: Artificial sequence
<220> FEATURE:
<223> OTHER INFORMATION: Synthetic peptide

<400> SEQUENCE: 12

Gly Gly Ser Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 13

Asp Xaa Ser Asp Glu
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide

<400> SEQUENCE: 14

Tyr Trp Thr Asp
1

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 15

Phe Asp Asn Pro Xaa Tyr
1               5
```

TREATMENT OF LIVER DISORDERS BY ADMINISTRATION OF RAP CONJUGATES

CROSS-REFERENCE TO RELATED APPLICATION

This application claims the benefit of prior filed International Application No. PCT/US06/36453, filed Sep. 18, 2006, hereby incorporated by reference.

FIELD OF THE INVENTION

The present invention relates to the use of receptor-associated protein (RAP), RAP fragments and RAP variants in methods for the treatment of liver disorders or conditions comprising administering RAP polypeptides conjugated to a therapeutic or active agent.

BACKGROUND OF THE INVENTION

LRP1 is a member of the low-density lipoprotein receptor "LDLR". LRP1 is a large protein of 4525 amino acids (600 kDa), which is cleaved by furin to produce two subunits of 515-(alpha) kD and 85-(β) kDa that remain non-covalently bound. LRP is expressed on most tissue types, but is primarily found in the liver. Other members of the low-density lipoprotein (LDL) receptor family include LDL-R (132 kDa); LRP2 (megalin, gp330); LRP/LRP1 and LRP1B (600 kDa); VLDL-R (130 kDa); LRP5; LRP6; apoER-2 (LRP-8, 130 kDa); Mosaic LDL-R (LR11, 250 KDa); and other members such as LRP3, LRP6, and LRP-7.

LRP1 is believed to be a multifunctional receptor. A binding repeat, resembling those found in the LDL receptor, is the molecular principle for the ability to bind a variety of ligands that were previously thought to be unrelated. These include the ligands lactoferrin, receptor associated protein (RAP), lipoprotein lipase, apoE, Factor VIII, beta-amyloid precursor, alpha-2-macroglobulin, thrombospondin 2 MMP-2 (matrix metalloproteinase-2), MPP-9-TIMP-1 (tissue inhibitor of matrix metalloproteinase-1); uPA (urokinase plasminogen activator):PAI-I (plasminogen activator inhibitor-1):uPAR (uPA receptor); and tPA (tissue plasminogen activator):PAI-1:uPAR, *Pseudomonas* exotoxin A, and human rhinovirus. See, Meilinger et al., FEBS Lett, 360:70-74 (1995). LRP1 is has the GenBank Accession No.: X 13916 and SwissProt Primary Accession No.: Q07954. Alternative names for the LRP1 gene/protein include: Low-density lipoprotein receptor-related protein 1 [precursor], LRP, Alpha-2-macroglobulin receptor, A2MR, Apolipoprotein E receptor, ApoER, CD91, LRP1 or A2MR.

An endoplasmic reticular chaperone protein, the receptor-associated protein (RAP), binds to complement repeat (CR) sequences within most LDLR. RAP assists in the folding of LDLR within the secretory pathway and antagonizes binding of all other known ligands to LDLR (Bu, (2001) Int Rev Cytol 209, 79-116). Despite the lack of detailed structural information on RAP, the association of RAP with the CR fold has been extensively characterized by a combination of receptor binding assays, calorimetry, and mutagenesis (Andersen, et al., (2001) Biochemistry 40, 15408-15417; Andersen, et al., (2000) J Biol Chem 275, 21017-21024; Migliorini, et al., (2003) J Biol Chem 278, 17986-17992; Neels, et al., (1999) J Biol Chem 274, 31305-31311; Horn, et al., (1997) J Biol Chem 272, 13608-13613)).

RAP is comprised of an array of three weakly homologous domains (Obermoeller, et al., (1997) J Biol Chem 272, 10761-10768). Each of these domains (d1, d2 and d3) has been shown to bind with varying affinity to pairs of immediately adjacent CR sequences within the LDLR ectodomains. Each of the effects of full-length RAP on LDLR, including facilitation of folding and inhibition of the binding of most other ligands (except α-2-macroglobulin), are recapitulated by RAPd3 alone. RAP d3 comprises amino acids 200-323 of mature Uniprot P30533 and amino acids 234-357 of precursor Uniprot P30533.

Hepatocytes are epithelial cells lining the vascular sinusoids of the liver. This cell type constitutes about 80% of total liver mass, providing the vast blood contact surface necessary for the function of the organ. Hepatocytes express large amounts of the low-density lipoprotein receptor-associated protein (LRP1), which participates in lipoprotein metabolism, specifically chylomicron remnant clearance (1,2,3), as well as uptake of other circulating proteins into the liver (2,4,5). Consistent with its physiological roles, LRP1 is a highly efficient ligand trafficking receptor, undergoing constitutive endocytosis with rapid internalization and recycling rates (6). Following internalization, LRP1 delivers bound cargo to the lysosome where the protein is rapidly degraded.

Hepatocellular carcinoma (HCC) originates from hepatocytes or their progenitors. HCC is the fifth most common cancer worldwide, the third most common cause of cancer-related death, and has shown increasing incidence in the U.S (7,8,9,10,11,12). The probability of developing hepatocellular carcinoma increases with viral infection (hepatitis B and C), alcoholism, smoking and obesity. Prognosis for this disease is poor, with a reported 5-year median survival rate of under 5%. Surgical resection, transplant and physical ablation are first choices for treatment, but only 5 to 10% of patients present with tumors suitable for these approaches. Tumor size, tumor dissemination within the liver, metastasis, diminished levels of organ function and high levels of recurrence limit the effectiveness of surgical intervention (13). Transarterial chemoembolism (a procedure in which the blood supply to a tumor is blocked (embolized) and chemotherapy is administered directly into the tumor) and intrahepatic chemotherapy (direct introduction of chemotherapy into liver tissue) have been shown to be helpful in some cases, but also give low overall rates of response (14,15). Systemic chemotherapy, such as adriamycin yields response rates of 15-20%, both because of the systemic toxicity of effective chemotherapeutics and tumor-cell resistance to the same (16, 17). As the majority of HCC cases occur in patients whose liver function is already compromised, effective chemotherapeutic regimens, most of which result in some hepatoxicity, are often contraindicated due to insufficient hepatic reserve and the risk of fulminant liver failure. Targeted delivery of conjugated therapeutics, such as $^{90}$Yttrium, to liver after intravenous administration would significantly reduce the systemic toxicities associated with these drugs, reducing risk to the patient during treatment of HCC. One method of providing this targeted delivery could employ liver specific molecules, or ligands that bound to receptors on the liver with high-affinity, such as RAP.

Thus, there is a need in the art to further abate patient risk by selective tumor targeting of therapeutics to the liver using high-affinity ligands, such as RAP-dependent blood-borne delivery of chemotherapeutics or other agents to hepatocellular locations, to treat liver carcinoma or other liver diseases.

SUMMARY OF THE INVENTION

The present invention relates to the use of RAP, RAP fragments and RAP variants for the treatment of liver disorders in a subject via administration of RAP-conjugated active agents which have improved transport into the liver.

In one aspect, the invention provides a method of treating a liver disorder in a subject comprising administering to said subject an effective amount of a conjugate comprising (a) a receptor binding moiety selected from the group consisting of Receptor Associated Protein of SEQ ID NO: 1 (RAP), RAP fragments, and RAP variants that retain RAP's binding affinity to LRP1 of about 1-5 nM, attached to (b) an active agent for treatment of liver disorder The RAP variant molecule may constitute a portion of full-length human RAP. In one embodiment the RAP variant is missing at least 200 and up to 243 amino acids from the N-terminus of SEQ ID NO: 1. In a related embodiment, the RAP fragment or variant is missing 243 amino acids from the N-terminus of SEQ ID NO: 1. In another embodiment, the RAP variant is missing up to 11 amino acids from the C-terminus, and may further be missing at least 4 amino acids from the C-terminus of SEQ ID NO: 1. In a further embodiment the RAP variant comprises a continuous portion of mature RAP (SEQ ID NO: 1) that is (a) at least 71 amino acids in length and (b) comprises amino acids 256-270. In a related embodiment, the RAP variant comprises a continuous portion of RAP d3 (SEQ ID NO: 2) that is (a) at least 71 amino acids in length and (b) comprises amino acids 256-270.

In one embodiment, the RAP variants have mutations within the third domain (d3) of RAP. RAP d3 comprises amino acids 200-323 of mature RAP (Uniprot P30533) (SEQ ID NO: 2) and amino acids 234-357 of precursor RAP (Uniprot P30533). In another embodiment, it is contemplated that the polypeptide comprises a RAP variant that lacks at least amino acids 1-143 of RAP of mature P30533. In a further embodiment, the RAP variant lacks at least amino acids 1-143 and amino acids 320-323 of mature RAP. In yet another embodiment, the polypeptide lacks up to 4 of the C-terminal amino acids of RAP of mature P30533.

In a related embodiment, the invention contemplates a method wherein the receptor binding moiety is a cyclic RAP peptide that is less than about 85 amino acids in length, comprising 50 contiguous amino acids that are at least 70% identical to SEQ ID NO: 4, and which binds to LRP1. In a related embodiment, the cyclic RAP peptide binds to LRP1 with a Kd of about $1 \times 10^{-8}$ M or less.

In another aspect, the invention provides methods wherein the RAP, RAP fragment or RAP variant comprises a mutation. In one embodiment, the mutation comprises one or more conservative substitutions relative to native RAP of SEQ ID NO: 1. In another embodiment, the mutation is the replacement of an acidic amino acid with a basic amino acid. In one embodiment, said acidic amino acid is selected from the group consisting of D and E. In a related embodiment, said basic amino acid is selected from the group consisting of K and R.

In a related aspect, said mutation in the RAP, RAP fragment or RAP variant is the replacement of a basic amino acid with an acidic amino acid. In one embodiment, said basic amino acid is selected from the group consisting of K and R. In another embodiment, said acidic amino acid is selected from the group consisting of D and E.

In a further embodiment, said mutation is the replacement of an amino acid selected from the group consisting of A, C, D, E, G, I, K, L, M, N, P, Q, R, S, T, and V with an amino acid selected from the group consisting of F, Y, W, and H. In a related embodiment, the RAP fragment or RAP variants contemplated for use in the invention comprise a mutation at any one of positions 251, 256, 257, 266, 270, 279, 280, 296 or 305 of mature RAP.

In addition to RAP variants alone, the invention contemplates oligomeric combinations of RAP domains or variants of RAP domains. The RAP coding sequence has been divided into the three, previously defined domains. Each domain comprises approximately 100 amino acids with a molecular mass of approximately 10 kD. Domain 1 (or d1) consists of amino acids 1-94 of the mature sequence of Genbank Accession No. P30533; domain 2 (or d2) consists of amino acids 95-198; and domain 3 (or d3) consists of amino acids 199-319, lacking the C-terminal 4 amino acid retention signal (SEQ ID NO: 9).

Thus, the invention contemplates that variants of RAP domains include polypeptides comprising 2 or more variants of RAP d1, comprising 2 or more variants of RAP d2, comprising 2 or more variants of RAP d3, comprising a variant of RAP d1 and variant of RAP d3 but lacking RAP d2, comprising 2 or more variants of RAP d1 together with 2 or more variants of RAP d2 or RAP d3 in various combinations (e.g. d1-d3, d1-d3-d3, d1-d1-d3, d1-d1-d3-d3, d1-d3-d1-d3, d1-d3-d1-d3-d1, d3, d1-d2-d1, d2-d2-d3, d3-d2-d3, d2-d3-d2-d3-d2-d3, etc), including consecutive repeats of the same sequence or alternating sequences, comprising multiple variants of RAP d1 and d2 in various combinations, or comprising multiple variants of RAP d2 and d3 in various combinations. The various combinations may be contiguous or separated by peptide linkers that display the domains in a 3-dimensional configuration that allows the domains to bind different CR pairs within the same CR-containing protein or to bind CR pairs of different CR-containing proteins.

Thus, in exemplary embodiments, the invention contemplates an oligomeric combination comprising 2 or more variants of RAP d3, wherein the variant of RAP d3 is a cyclic RAP peptide as described herein.

The invention further contemplates use of a conjugate comprising the polypeptide receptor-associated protein (RAP), RAP variant, RAP fragment or combination of variants, conjugated to a diagnostic or therapeutic agent. In one embodiment, the polypeptide and diagnostic or therapeutic agent are linked through a linker. In a further embodiment, said linker is a peptide linker.

In a related aspect, the invention provides for use of a pharmaceutical composition comprising a RAP variant conjugated to a diagnostic or therapeutic agent in a pharmaceutically acceptable carrier, diluent or excipient.

In another aspect, the present invention provides a method to produce RAP variants and conjugates in amounts which enable using compositions comprising such RAP variants and RAP conjugates therapeutically. The invention also provides a nucleic acid that encodes any of the foregoing polypeptides comprising RAP, RAP fragments and RAP variants useful in the methods of the invention. Vectors comprising such nucleic acids, host cells containing such nucleic acids or vectors, and methods of producing such polypeptides comprising the steps of culturing the host cells in suitable culture medium and isolating the polypeptide from said host cells or culture medium are also provided.

In one aspect, the invention provides methods for treatment of a disease or condition associated with liver damage, wherein the liver condition or disease is selected from the group consisting of hepatic cancer, hepatitis, cirrhosis, fungal, rickettsial or parasitic infections, damage associated with alcohol, chemical toxins, and drug toxicity, metabolic liver disease, idiopathic autoimmune liver disease, biliary obstruction, hepatic steatis, cholestasis, and post-hepatectomy conditions. In one embodiment, the hepatic cancer is Hepatocellular carcinoma.

In a related embodiment, the hepatic cancer is selected from the group consisting of hepatocellular carcinoma and the active agent moiety is a cytotoxic chemotherapeutic agent.

In a further embodiment, the disorder is a liver tumor or tumor metastases in the liver, and the therapeutic agent is a chemotherapeutic agent.

In one aspect, the invention provides a method for treatment wherein the active agent is a cytotoxic agent. In one embodiment, the cytotoxic agent is selected from the group consisting of Mechlorethamine hydrochloride, Cyclophosphamide, Ifosfamide, Chlorambucil, Melphalan, Busulfan, Thiotepa, Carmustine, Lomustine, Dacarbazine and Streptozocin.

In a related aspect, the cytotoxic agent is a radioisotope. In related embodiment, the radioisotope is selected from the group consisting of $^{131}I$, $^{125}I$, $^{111}In$, $^{90}Y$, $^{67}Cu$, $^{127}Lu$, $^{212}Bi$, $^{213}Bi$, $^{255}Fm$, $^{149}Tb$, $^{223}Rd$, $^{213}Pb$, $^{212}Pb$, $^{211}At$, $^{89}Sr$, $^{153}Sm$, $^{166}Ho$, $^{225}Ac$, $^{186}Re$, $^{67}Ga$, $^{68}Ga$ and $^{99m}Tc$.

In a still further aspect, method of the invention provides that the disorder to be treated is hepatitis caused by a virus, and the therapeutic agent is an antiviral agent.

BRIEF DESCRIPTION OF THE DRAWINGS

FIG. 1A illustrates binding of RAP d3 mutants and RAPv2A d3 revertants to LRP2 CR89. FIG. 1B illustrates binding of RAP d3 mutants and RAPv2A d3 revertants to LRP1 CR3-5. Data were plotted and fitted by non-linear regression with the assumption of a single binding site (GraphPad Prism). Kd values with standard deviations were derived from the regression analysis.

Figure 1A:
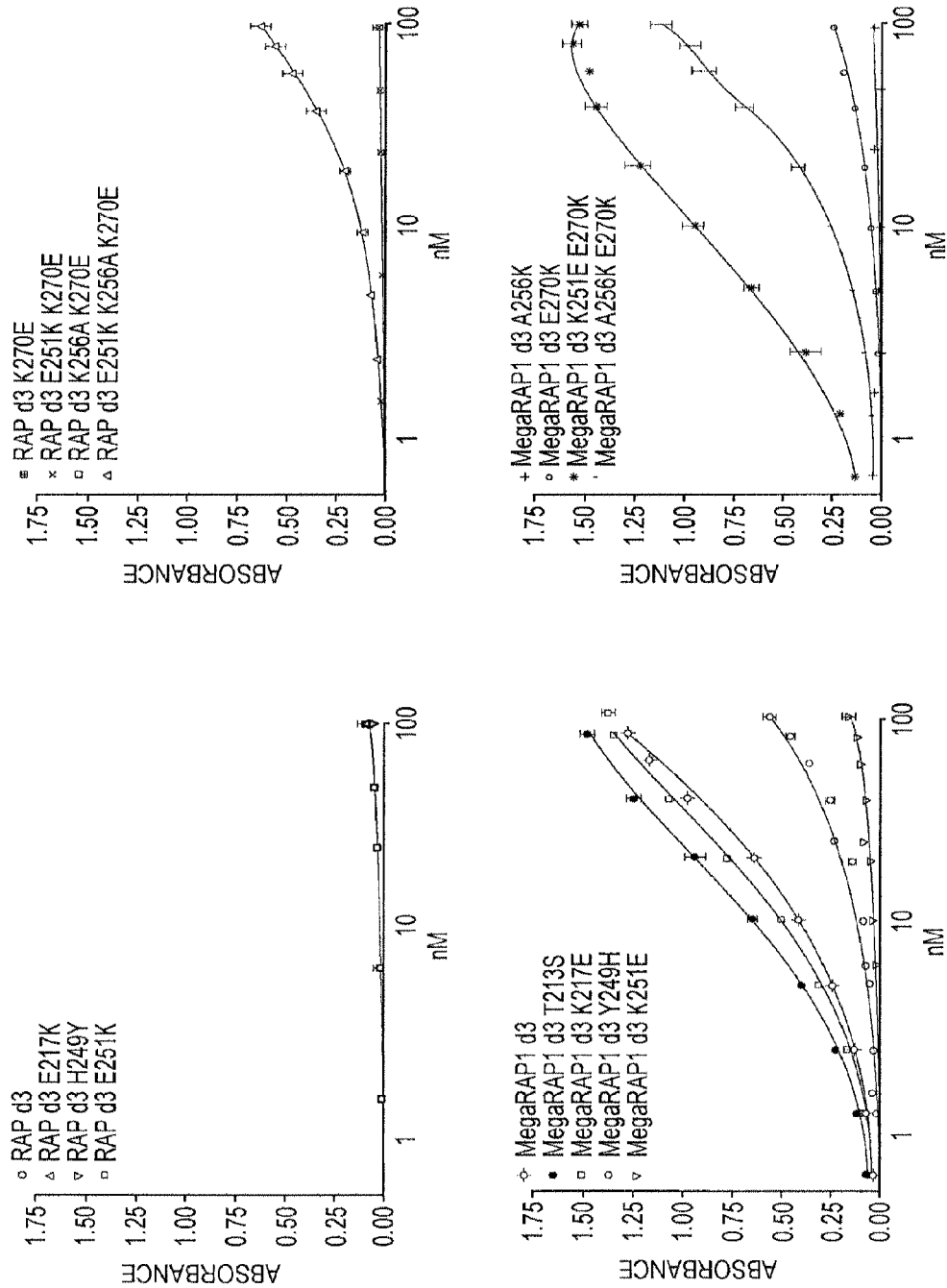
FIG. 1A-B depict binding of RAP d3, MegaRAP1 d3 (RAPv2A d3) and intermediate sequence variants to LRP2 CR89 and LRP1 CR3-5.

Table 2 shows data for binding of RAP d3 and RAP v2 (RAP v2A) variants to LRP1 CR3-5 and LRP2 CR89. NF indicates that binding could not be measured or that data could not be reliably fit using non-linear regression with the assumption of a single binding site. Percent of maximum binding is the ratio of the OD at the highest concentration tested for each ligand and the highest OD measured for all such ligands at that concentration.

DETAILED DESCRIPTION

The present invention relates to methods of delivering compounds to the liver comprising administering RAP protein conjugates that bind to liver receptor LRP1 and are internalized into the liver. Internalization of the RAP-conjugate is an effective means of delivering therapeutic compounds or other active agents to the liver to treat a liver disease or condition.

A. DEFINITIONS

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

"Liver tumors and other neoplasia in or around the liver" as used herein includes both primary tumors and/or metastases that develop in or around the liver. It may also mean metastases of liver tumors that migrate elsewhere in the body, but remain responsive to RAP, RAP fragments or RAP variant polypeptide conjugates with chemotherapeutic agents. Many types of such tumors and neoplasia are known. Primary liver tumors include hepatocellular carcinoma and others known in the art. As used herein, tumors and neoplasia may be associated with the liver and hepatic tissue. Such tumors are generally solid tumors, or they are diffuse tumors with accumulations localized to the liver. Tumors or neoplasia for treatment according to the invention may be malignant or benign, and may have been treated previously with chemotherapy, radiation and/or other treatments.

The term "effective amount" means a dosage sufficient to produce a desired result on a health condition, pathology, and disease of a subject or for a diagnostic purpose. The desired result may comprise a subjective or objective improvement in the recipient of the dosage. "Therapeutically effective amount" refers to that amount of an agent effective to produce the intended beneficial effect on health.

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5,000 Da, up to about 2,000 Da, or up to about 1,000 Da.

A "subject" of diagnosis or treatment is a human or non-human animal, including a mammal or a primate.

"Treatment" refers to prophylactic treatment or therapeutic treatment or diagnostic treatment.

A "prophylactic" treatment is a treatment administered to a subject who does not exhibit signs of a disease or exhibits only early signs for the purpose of decreasing the risk of developing pathology. The conjugate compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective. The conjugate compounds of the invention may be given as a therapeutic treatment or for diagnosis.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a pharmacologically effective amount of a RAP, RAP fragment or RAP variant polypeptide conjugated to an active agent, and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a conjugate compound of the present invention and a pharmaceutically acceptable carrier.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular conjugate employed and the effect to be achieved, and the pharmacodynamics associated with each compound in the host.

"Modulate," as used herein, refers to the ability to alter, by increase or decrease (e.g., to act as an antagonist or agonist).

"Increasing relative delivery" as used herein refers to the effect whereby the accumulation at the intended delivery site (e.g., liver) of a RAP, RAP fragment or RAP variant-conjugated active agent is increased relative to the accumulation of the unconjugated active agent.

"Therapeutic index" refers to the dose range (amount and/or timing) above the minimum therapeutic amount and below an unacceptably toxic amount.

"Equivalent dose" refers to a dose, which contains the same amount of active agent.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T." Nucleotide sequences that encode proteins and RNA may include introns.

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer).

A "Complement-repeat" or "CR", also known as a low-density lipoprotein receptor class A domain (LDL-A, Pfam), is a member of a family of protein domains defined by six cysteines and a cluster of acidic amino acids, among other features. A number of complement-repeats have been found to fold into a defined structure termed the LDL receptor-like module (Structural Classification of Proteins, SCOP). CR domains constitute the ligand-binding determinant of many receptors, including receptors belonging to the LDLR. A linear sequence of amino acids within each CR, with the motif AxcBxCxD, where c is a conserved cysteine, x is any amino acid, and B and D are either aspartate, glutamate or asparagine, has been demonstrated to participate in calcium binding and in the binding of ligands. Immediately adjacent pairs of particular CR domains have been demonstrated to bind to RAP. Amino acids at positions A and C in both of the two CR domains of a RAP-binding CR pair (A, C, A' and C') have been demonstrated to participate in RAP binding.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is expressed in the recombinant host cell to produce, e.g., a "recombinant polypeptide." A recombinant polynucleotide may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

"RAP variant" refers to any of two or more polymorphic forms of alpha-2-macroglobulin/low density lipoprotein receptor-related protein-associated protein 1 (RAP), Uniprot accession P30533, Pfam accession numbers PF06400 and PF06401). Variants differ in the composition of their amino acid sequences based on one or more mutations involving substitution of one or more amino acids for other amino acids. Substitutions can be conservative or non-conservative based on the physico-chemical or functional relatedness of the amino acid that is being replaced and the amino acid replacing it.

The terms "identical" or "percent identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially homologous" or "substantially identical" in the context of two nucleic acids or polypeptides, generally refers to two or more sequences or subsequences that have at least 40%, 60%, 80%, 90%, 95%, 98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of either or both comparison biopolymers.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm calculates the percent sequence identity for the test sequence(s) relative to the reference sequence, based on the designated program parameters.

Optimal alignment of sequences for comparison can be conducted, e.g., by the local homology algorithm of Smith and Waterman, Adv. Appl. Math. 2:482 (1981), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. Another example of algorithm that is suitable for determining percent sequence identity and sequence similarity is the BLAST algorithm, which is described in Altschul et al., J. Mol. Biol. 215:403-410 (1990).

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the conjugates of the invention are substantially pure or isolated. In some embodiments, the conjugates useful in the methods of the invention are substantially pure or isolated with respect to the macromolecular starting materials used in their synthesis. In some embodiments, the pharmaceutical composition of the invention comprises a substantially purified or isolated conjugate of a RAP, RAP fragment or RAP variant polypeptide and the active agent admixed with one or more pharmaceutically acceptable excipient.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

B. LDLR

"LDLR" refers to members of the low-density lipoprotein receptor family including the low-density lipoprotein receptor-related protein 1 (LRP1), LDL-R (132 kDa); LRP2 (megalin, gp330); LRP/LRP1 and LRP1B (600 kDa); VLDL-R (130 kDa); LRP5; LRP6; apoER-2 (LRP-8, 130 kDa); Mosaic LDL-R (LR11, 250 KDa); and other members such as LRP3, LRP6, and LRP-7.

Characteristic features of the family include cell-surface expression; extracellular ligand binding domain repeats (Dx-SDE) (SEQ ID NO: 13); a requirement of Ca++ for ligand binding; binding of RAP and apoE; EGF precursor homology domain repeats (YWTD) (SEQ ID NO: 14); a single membrane spanning region; internalization signals in the cytoplasmic domain (FDNPXY) (SEQ ID NO: 15); and receptor mediated endocytosis of various ligands. Some members of the family, including LRP1, participate in signal transduction pathways.

LDLR ligands refer to a number of molecules that are known to bind LDLR. These molecules include, for instance, lactoferrin, RAP, lipoprotein lipase, apoE, Factor VIII, beta-amyloid precursor, alpha-2-macroglobulin, thrombospondin 2 MMP-2 (matrix metalloproteinase-2), MPP-9-TIMP-1 (tissue inhibitor of matrix metalloproteinase-1); uPA (urokinase plasminogen activator):PAI-I (plasminogen activator inhibitor-1):uPAR (uPA receptor); and tPA (tissue plasminogen activator):PAI-1:uPAR.

LDLR bind to a wide variety of extracellular ligands through conserved protein domains within the N-terminal extracellular domain, or ectodomain, of each receptor. These domains include the complement-type repeat (CR, or low-density lipoprotein receptor domain class A, ldl-a), the EGF-like repeat and the YWTD (SEQ ID NO: 14), or beta-propeller, domain. The CR domains are responsible for association with most of the ligands that have been identified. The CR sequence specifies a conserved fold, termed the LDL receptor-like module (SCOP terminology). Each approximately 36 amino acid CR contains six cysteines that form three intramolecular cystines in a 1-3, 2-5, 4-6 configuration, and a calcium ion bound within one lobe of a bilobate loop.

In LRP1, the second ligand-binding domain of human LRP1 is composed of eight consecutive CR units. Each of the seven possible adjacent CR pairs have been individually expressed and assayed for binding to RAPd3 (Andersen, et al., (2000) J Biol Chem 275, 21017-21024). Except for the last pair (CR9 and CR10), which contains non-preferred residues at CR positions in the second CR, all pairs bind with similar affinity (1-5 nM) to RAP.

C. RAP FRAGMENTS AND RAP VARIANTS

Figure 1B:
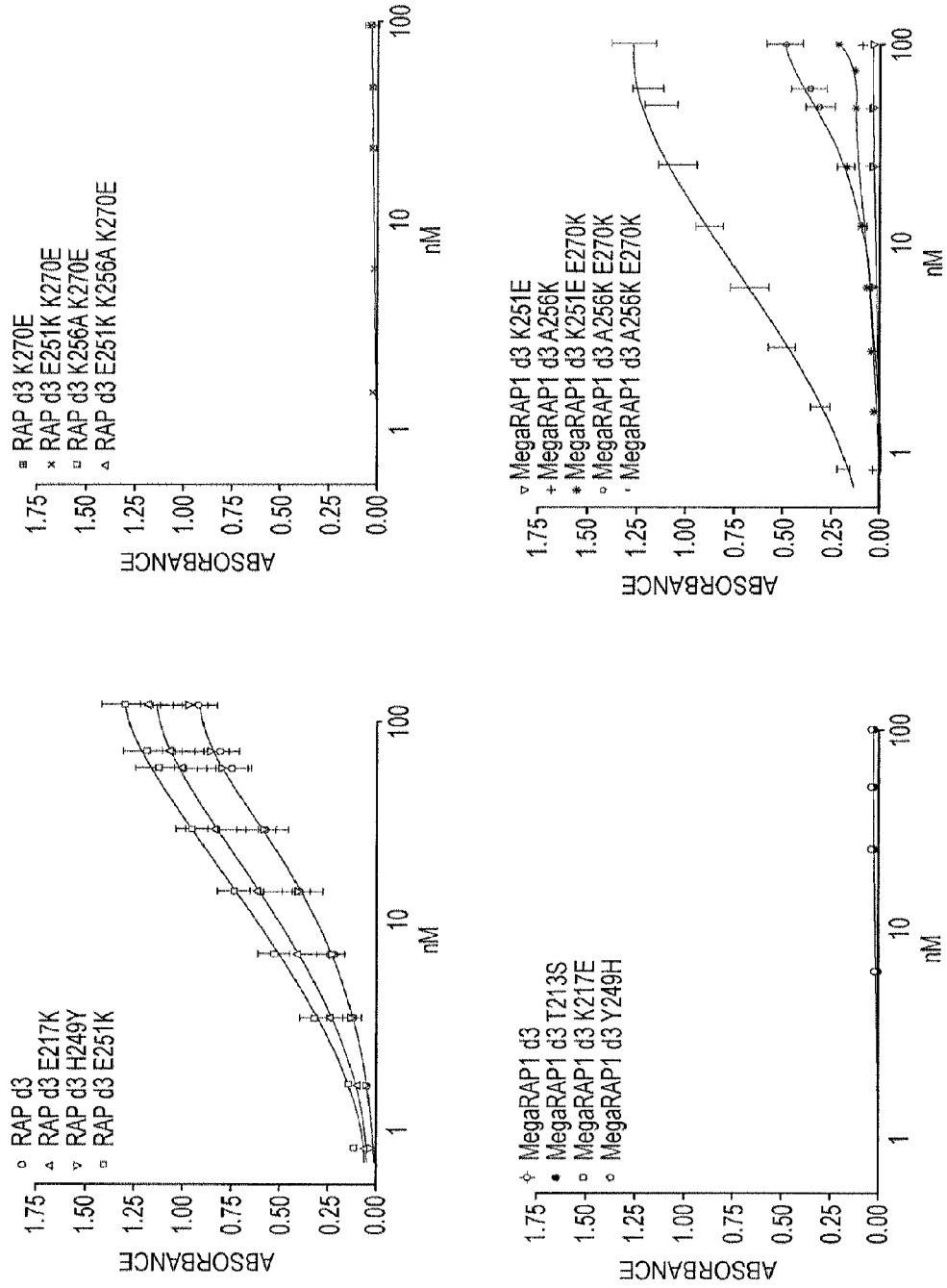

Random and site-directed mutagenesis of RAP indicates that there may be a few residues that contribute disproportionately to the affinity of the ligand complex with the CR pair (Migliorini, et al., (2003) J Biol Chem 278, 17986-17992). In particular, lysines at positions 256 and 270 in RAPd3 have been found to be important for binding of this domain to LRP1. For example, a RAPd3 variant termed Mega RAP1, which has mutations of H249T, E251K, K256A and K270D (based on full-length RAP sequence), fails to bind LRP1 CR domains (See FIG. 1, Table 2). Also important are two, discrete, ten amino acid basic regions centered on positions 205 and 285, respectively (Melman, et al., (2001) J Biol Chem 276, 29338-29346). These observations are consistent with there being a limited set of residues, a "hot-spot", that contribute the majority of binding energy between RAP and CR pairs, a phenomenon observed in other protein-protein interfaces (Li, et al, (2005) Structure (Camb) 13, 297-307; Halperin, et al., (2004) Structure (Camb) 12, 1027-1038; Gao, et al., (2004) J Mol Model (Online) 10, 44-54; Dwyer, et al., (2001) Biochemistry 40, 13491-13500; DeLano, (2002) Curr Opin Struct Biol 12, 14-20; Bogan, et al., (1998) J Mol Biol 280, 1-9; Clackson, et al., (1995) Science 267, 383-386).

The RAP molecule is initially produced as a 357 amino acid protein (SEQ ID NO: 6 and 7) having a 35 amino acid signal sequence which is cleaved to form mature RAP which is a 323 amino acid peptide (SEQ ID NO: 1). The mature RAP also retains a 4 amino acid C-terminal endoplasmic reticulum retention signal.

Substantial guidance exists in the art to which portions of RAP are important to its LRP binding and modulatory activity and which portions may be mutated, altered, or deleted without loss of binding activity (see, Nielsen et al. Proc. Nat. Acad. Sci. USA 94:7521 (1997); and Rall et al. J. Biol. Chem. 273(37):24152, 1998). For instance, RAP's LRP binding function has been mapped by performing direct binding studies on fusion proteins representing overlapping domains of RAP (see Willnow et al., J. Biol. Chem. 267(36):26172-80, 1992). The RAP binding motifs have also been characterized by use of truncated and site-directed RAP mutants (see Melman et al. J. Biol. Chem. 276(31):29338-29346, 2001). Particular RAP polypeptide fragments, suitable for use according to the invention, include fragments (defined from RAP N terminus amino acid to RAP C-terminus amino acid position) 1-323 (RAP); 1-319; 1-250; 1-110; 91-210; 191-323; 221-323; 1-190; 1-200; and 1-210. In one aspect, a RAP protein for use in the invention is mature RAP lacking the signal peptide (SEQ ID NO: 1), In a related aspect, the RAP lacks both the RAP signal peptide at the N-terminus and the HNEL endoplasmic reticulum retention signal at the C-terminus (SEQ ID NO: 8). Preferred RAP polypeptides include fragments 1-323 (RAP); 1-319; 191-323; and 1-210, fragments having at least 71 consecutive amino acids of RAP comprising amino acids 256-270, and RAP fragments having at least 71 consecutive amino acids of RAP comprising amino acids 256-270 and comprise a continuous portion of RAP d3. A modified RAP polypeptide having the C-terminal four amino acid sequence substituted by the sequence KDEL is also suitable. A modified RAP polypeptide in which the C-terminal-four amino acid sequence (HNEL) is deleted is also suitable. Also preferred are RAP polypeptides fragments that comprise the native sequence of RAP from amino acid 201 to 210.

RAP variants may also include conservative substitution of particular amino acid residues. "Conservative" amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E). The variation may be introduced by systematically making substitutions of amino acids in a polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for expressing polypeptide compositions useful in the invention are described in greater detail below.

Other preferred embodiments, comprise a human or mammalian RAP polypeptide in which the polypeptide comprises the native amino acid sequence of RAP over positions 282-289, 201-210, and 311-319. Mutated and N-terminus or C-terminus truncated variants of RAP which bind to the LRP receptor are disclosed in Melman et al. (J. Biol. Chem. 276 (31): 29338-46, 2001) which is incorporated herein by reference in its entirety and with particularity to these RAP mutated and truncated variants. Other preferred RAP polypeptides comprise a native sequence of RAP between amino acids 85-148 and 178-248. (See Farquhar et al., Proc. Nat. Acad. Sci. USA 91:3161-3162 (1994).

Thus, many references disclose the binding sites and structure activity relationships for binding of RAP and RAP fragments to the LRP receptor. The skilled artisan can readily adapt a variety of well known techniques in the art in order to obtain RAP polypeptides that contain a LRP binding site and are suitable for use as RAP polypeptides according to the invention. The preferred fragments of RAP are soluble under physiological conditions. The N-terminus or C-terminus of these polypeptides can be shortened as desired, provided that the binding capacity for the LRP particle remains intact.

D. CYCLIC RAP PEPTIDES

RAP is functionally bidentate, with both the first and third domains (d1 and d3) binding with low nanomolar affinity to particular tandem pairs of complement-type repeats (CR) within the LDLR (27). Domain 3, consisting of approximately 110 amino acids, has been shown to have the highest affinity for relevant CR pairs. To minimize immunogenicity, maximize production efficiency and improve potency, it is useful to minimize RAP to those sequences that participate directly in receptor binding. However, stable folding of d3 has been shown to require sequences within RAP that do not participate directly in forming the receptor contact surface (28). These additional sequences, found within the N-terminal region of d3 and the C-terminal region of d2, are therefore necessary to ensure stable folding and high-affinity receptor binding. Isolated d3 does not bind as tightly to receptor as does d3 within the context of full-length RAP. Truncated versions of d3 that lack the fold-stabilizing sequences also bind poorly to receptor. Structural data derived from the complex between RAP d3 and LDLR CR34 (29) indicates that the receptor-binding sequences of RAP d3 are found within two anti-parallel alpha-helices of approximately equal length joined by a flexible loop. The paired helical ensemble has a pronounced counter-clockwise twist and resembles a stretched, twisted "U".

A non-native disulfide bond has been engineered connecting the termini of the two anti-parallel helices making up the receptor binding unit of RAP d3 (See co-owned U.S. patent application No. 60/919,238, filed Mar. 21, 2007), the disclosure of which is incorporated by reference herein in its entirety. The cyclized peptide is approximately 75 amino acids long but has superior binding affinity compared to uncyclized peptide and comparable affinity to 110-amino acid RAP d3. One possible application for such minimized RAP d3 peptides is as a targeting agent for delivering therapeutic agents according to the methods of the invention.

The cyclic RAP peptides contemplated by the invention are based on the amino acid sequence of mature RAP, preferably domain 3, are preferably less than 123 amino acids in length and contain a covalent bond between two non-consecutive amino acids. In some embodiments, the covalent bond stabilizes the three-dimensional structure of the RAP peptide. In some embodiments, the covalent bond provides an improvement in binding affinity so that the cyclic RAP peptide binds to a CR-containing protein with a Kd of about $1 \times 10^{-8}$ M or less (less meaning better affinity). Such binding affinities can be measured by any method known in the art, such as radioimmunoassay, ELISA, surface plasmon resonance (SPR) based technology (e.g., Biacore) analysis, or kinetic exclusion assay (e.g., KinExA). The affinity data may be analyzed, for example, by the method of Scatchard et al., Ann N.Y. Acad. Sci., 51:660 (1949). In exemplary embodiments, the binding affinity for a CR-protein, such as LRP1, is about $1 \times 10^{-9}, 10^{-10}, 10^{-11}, 10^{-12}, 10^{-13}, 10^{-14}$ M or less. The invention provides cyclic RAP peptides of various sizes, including about 103, about 99, about 95, about 90, about 85, about 82, about 80, about 78, about 76, 75, 74, 73, 72, 71, 70, 69, 68, 67, 66, 65, 64, 63, 62, 61, 60, 59, 58, 57, or 56 amino acids in length or less. In some embodiments, the covalent bond is formed between amino acids that are separated by about 76, 75, 74, 73, 72, 71, 70, 69, 68, 67, 66, 65, 64, 63, 62, 61, 60, 59, 58, 57, or 56 amino acids.

In one embodiment the amino acid sequence of the RAP peptides (including cyclic RAP peptides) useful in the methods of the invention is missing at least 200 and up to 243 amino acids from the N-terminus of mature RAP. Thus, the RAP peptide may be missing amino acids 1-200, 1-220, 1-225, 1-230, 1-235, 1-240, 1-241, 1-242, 1-243, or alternatively 1-244, 1-245, 1-246, 1-247, or 1-248 of mature RAP. In a related embodiment, the RAP peptide amino acid sequence is further missing at least 4 and up to 11 amino acids from the C-terminus of mature RAP. Thus, the RAP peptide may be missing amino acids 314-323 or 313-323, or alternatively 304-323, 305-323, 306-323, 307-323, 308-323, 309-323, 310-323, 311-323, or 312-323 of mature RAP. In another embodiment the RAP peptide amino acid sequence comprises a continuous portion of mature RAP that is (a) at least 71 amino acids in length and (b) comprises amino acids 256-270. In a related embodiment, the RAP peptide amino acid sequence comprises a continuous portion of mature RAP domain 3 that is (a) at least 71 amino acids in length and (b) comprises amino acids 256-270. Exemplary portions of RAP which may form the basis for a RAP peptide (including cyclic RAP peptide) include amino acids 200-323, 221-323, 200-319, 221-319, 243-319, 244-319, 249-319, 200-313, 221-313, 243-313, 244-313, 249-313, 200-303, 221-303, 243-303, 244-303, or 249-303 of mature RAP (SEQ ID NO: 1).

As described herein, cyclic RAP peptides can be prepared that exhibit affinity for and selectivity for CR-containing proteins that is similar to that of native RAP (e.g., about 5-fold difference or less compared to native RAP). Cyclic RAP peptides can also be prepared that exhibit improved affinity for LRP1 compared to native RAP. In one embodiment, the cyclic RAP peptide exhibits at least 1.5-fold, 2-fold, 2.5-fold, 3-fold, 4-fold, 5-fold, 7-fold, 10-fold, or 20-fold improved affinity (relative to native RAP) for LRP1 (P98157).

The cyclic RAP peptides contemplated by the invention may be composed of native RAP sequence or may include mutations to the native sequence. In exemplary embodiments, the cyclic RAP peptides of the invention comprise an amino acid sequence at least 60%, 65%, 70%, 75%, 80%, 85%, 90%, 91%, 92%, 93%, 94%, 95%, 96%, 97%, 98% or 99% identical to either amino acids 243-313 of RAP set forth in SEQ ID NO: 3 or amino acids 249-303 of RAP set forth in SEQ ID NO: 4. In some embodiments, the cyclic RAP peptide is less than about 85 amino acids in length, comprises 50 contiguous amino acids that are at least 70% identical to SEQ ID NO: 4, and binds to a CR-containing protein with a binding affinity Kd of about $1\times10^{-8}$ M or less.

Cyclic RAP peptides may be made that contain conservative substitutions (e.g., up to 5, up to 10, up to 15, up to 20 or up to 25) relative to the native RAP sequence yet still retain binding affinity for LRP1. RAP peptides containing non-conservative substitutions may also retain binding affinity for LRP1. For example, a non-conservative mutation at any one of positions 217, 249, or 251 of mature RAP has been shown not to affect binding affinity.

In any of the preceding embodiments, the RAP peptides may contain a cysteine at or near the N-terminus of the peptide and a cysteine at or near the C-terminus of the peptide, allowing cyclization of the peptide and stabilization of the alpha-helices through disulfide bond formation between the two cysteines. Optionally, a glycine or proline may be interposed between the cysteines and the alpha-helices (e.g. Cys-Gly at the N-terminus and Gly-Cys at the C-terminus). Introduction of glycines allows a break in the alpha-helix for an adjacent non-native inter-helical disulfide bond.

The cyclic peptide, Hep1, is stabilized by a non-native internal disulfide bond, which improves binding thermodynamics (Kd>50 nM to Kd<1 nM), presumably by diminishing entropic losses upon complex formation between the peptide and LRP1. Additional RAP variants which bind to LRP1 and useful for treatment of liver disease are described in co-owned International Patent Application No. PCT/US2006/36453, incorporated herein by reference in its entirety.

The Hep1 sequence differs from human RAP at three positions at the N-terminus (LEA/XCG) and two positions at the C-terminus (RI/GC) (SEQ ID NO: 9). Patients should be immunologically tolerant of peptides derived from RAP. While an epitope within domains 1 and 2 of RAP plays a role in the development of experimental Heymann nephritis in rats, the Hep1 peptide is derived entirely from domain 3. Since human RAP has sequence differences with both rodent and canine RAP sequences, these species are expected to develop significant anti-drug antibody titers within a few weeks of intravenous administration.

Figure 3:
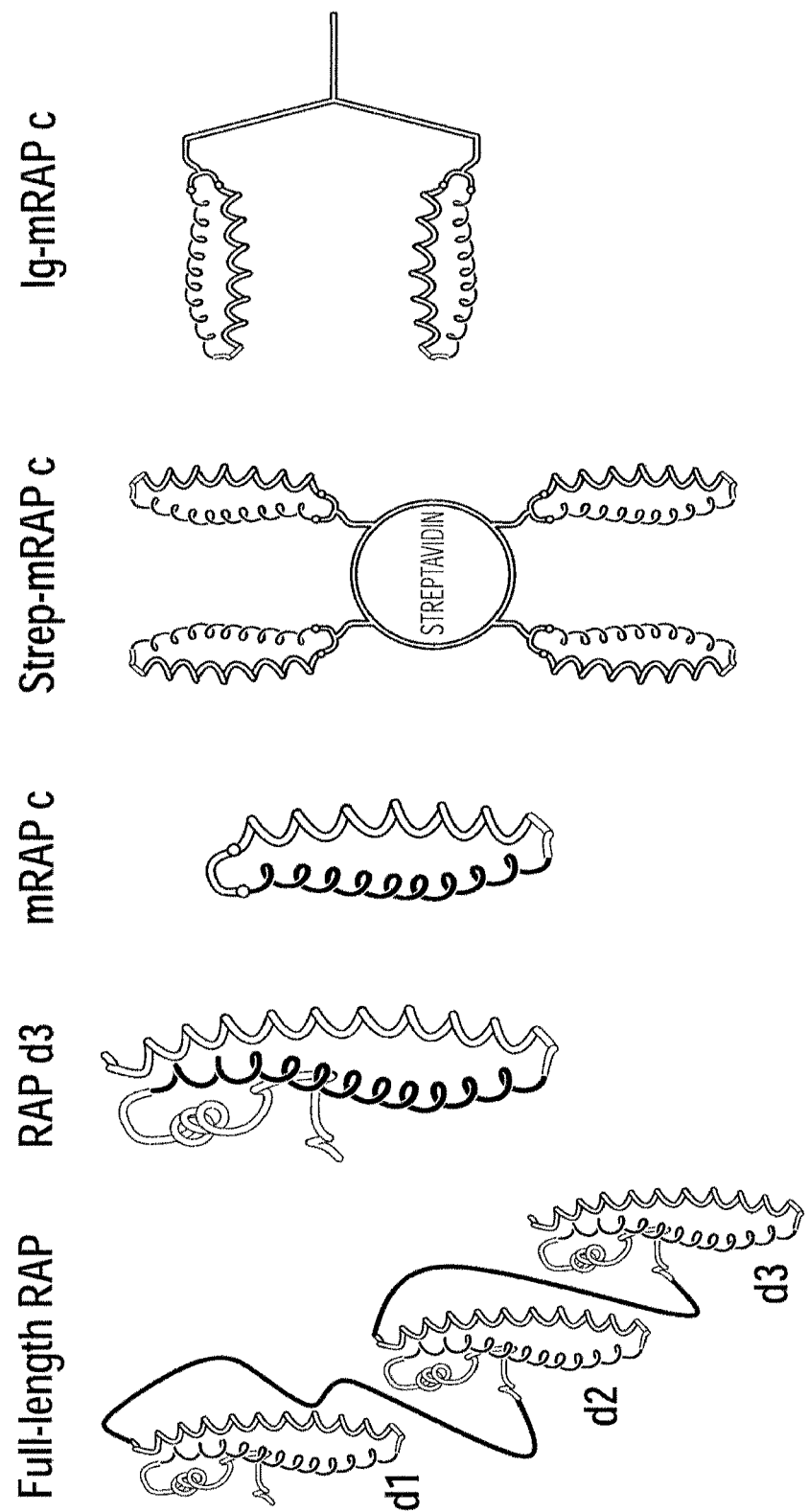
FIG. 3 is an illustration of the structure of cyclic RAP and multimerized cyclic RAP peptides.
Figure 4:
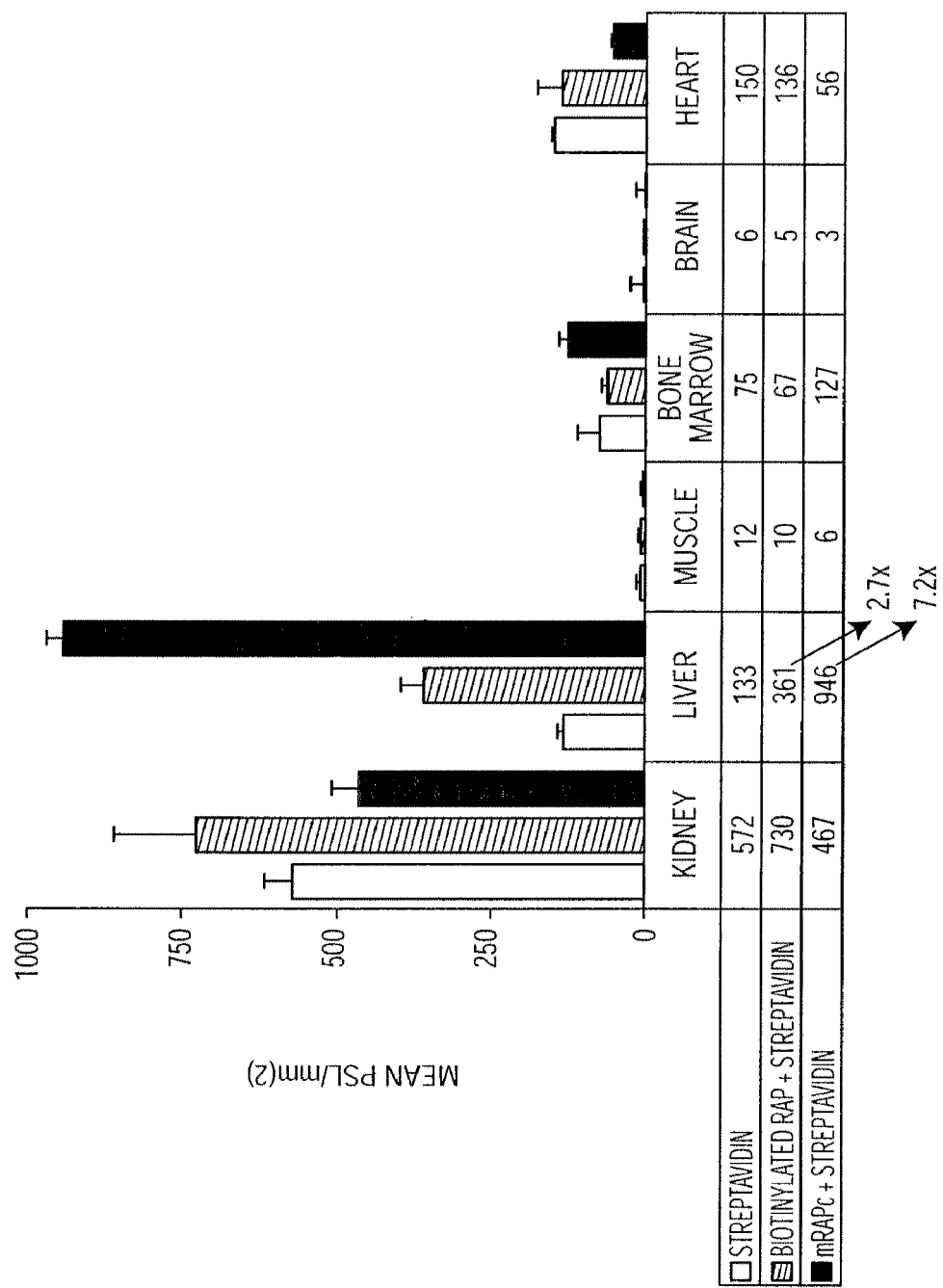
FIG. 4 shows the uptake and bio-distribution of mRAPc multimerized peptides in tissues in vivo.

It is further contemplated that any of the cyclic RAP peptides herein are multimerized into oligomeric combinations as described herein. "Multimerized cyclic RAP peptide" as used herein refers to a polypeptide comprising 2 or more variants of RAP d3, wherein the variant of RAP d3 is a cyclic RAP peptide as described herein. The terms "multimer" and "oligomer" are used interchangeably herein. In one embodiment, the oligomer or multimer comprises at least two, at least three, at least four, at least five, at least six, at least seven or at least eight cyclic RAP peptides. In one exemplary embodiment, the cyclic RAP peptides are conjugated to a biotin molecule in order to facilitate multimerization or oligomerization. The biotin-conjugated-cyclic peptides may then be multimerized by binding to streptavidin or by binding to an anti-biotin antibody (FIG. 3). Cyclic RAP peptide oligomers or multimers may also be made by other techniques well-known in the art and described below.

A number of techniques are known in the art to create multimers or oligomers of peptides. For example, peptides can be linked by linkers as described herein or via polyethylene glycol. See Zhang et al., Bioconjug Chem. 14:86-92, 2003 (amyloid fibril-binding peptides connected by either a poly(ethylene glycol) (PEG) spacer or just two amino acids displayed about 100-fold greater affinity for fibrils, while placing six copies of the peptide on a branched PEG resulted in a 10000-fold greater affinity), incorporated by reference herein in its entirety. Peptides can be readily multimerized after biotinylation through coupling to streptavidin. See, e.g., Guillaume et al., J. Biol. Chem., 278(7): 4500-4509, 2003 (peptide multimers can be prepared by linkage via avidin or avidin derivatives, and homogeneous preparations of tetramers and octamers are possible), incorporated by reference herein in its entirety. Peptides with receptor-binding capabilities can be grafted into different CDR regions of an antibody or immunoglobulin scaffold. See Frederickson et al., Proc Natl Acad Sci USA. 103(39):14307-12, 2006. Epub Sep. 14, 2006 (antibodies and fragments containing two grafted mpl receptor-binding peptides stimulated mpl receptor in a manner estimated to be equipotent to the native ligand), incorporated by reference herein in its entirety. Peptides may be attached in tandem or branched fashion, with or without linkers, to antibody Fc domains. See Intl Publication No. WO 00/24782, published May 4, 2000, incorporated by reference herein in its entirety. Peptides and other proteins may be displayed on a macromolecular scaffold derived from a multienzyme complex. See Domingo et al., J Mol. Biol. 305(2): 259-67, 2001, incorporated by reference herein in its entirety. For a review of protein scaffolds suitable for displaying peptides, see Hosse et al., Protein Science 15:14-27, 2006 (reviewing scaffolds such as the fibronectin type III domain, a lipocalin, a knottin, cytochrome b562, a kunitz-type protease inhibitor, the Z-domain, and the carbohydrate binding module CBM4-2), incorporated by reference herein in its entirety.

Thus, in exemplary embodiments, bivalent oligomeric combinations are made by homodimerization of a polypeptide comprising a cyclic RAP peptide and an antibody Fc region. Tetravalent oligomeric combinations are made by replacing antibody variable regions in a tetrameric immunoglobulin (containing two heavy chains and two light chains) with a cyclic RAP peptide. In yet other exemplary embodiments, bivalent, trivalent, tetravalent, or other oligomeric combinations are made by conjugation of cyclic RAP peptide to a PEG molecule. Other oligomeric combinations can be envisioned by those of ordinary skill in the art.

E. CONJUGATES OF RAP, RAP FRAGMENTS OR RAP VARIANTS AND ACTIVE AGENT

A "RAP conjugate", "ligand-polypeptide conjugate" "chimeric molecule comprising a RAP, RAP fragment or RAP variant conjugated to an active agent" each refers to a compound comprising a RAP, RAP fragment or RAP variant attached to an active agent. As used herein, the term "conjugated" means that the therapeutic agent(s) and RAP, RAP fragment or RAP variant polypeptide are physically linked by, for example, by covalent chemical bonds, physical forces such van der Waals or hydrophobic interactions, encapsulation, embedding, or combinations thereof. In preferred embodiments, the therapeutic agent(s) and the RAP, RAP fragment or RAP variant polypeptide are physically linked by covalent chemical bonds. As such, preferred chemotherapeutic agents contain a functional group such as an alcohol, acid, carbonyl, thiol or amine group to be used in the conjugation to RAP, RAP fragment or RAP variant or fragment thereof. Adriamycin is in the amine class and there is also the possibility to link through the carbonyl as well. Paclitaxel is in the alcohol class. Chemotherapeutic agents without suitable conjugation groups may be further modified to add such a group. All these compounds are contemplated in this invention. In the case of multiple therapeutic agents, a combination of various conjugations can be used.

In some embodiments, a covalent chemical bond that may be either direct (no intervening atoms) or indirect (through a linker e.g., a chain of covalently linked atoms) joins the RAP, RAP fragment or RAP variant and the active agent. In preferred embodiments, the RAP, RAP fragment or RAP variant and the active agent moiety of the conjugate are directly linked by covalent bonds between an atom of the RAP, RAP fragment or RAP variant and an atom of the active agent. In some preferred embodiments, the receptor binding moiety is connected to the active agent moiety of the compound according to the invention by a linker that comprises a covalent bond or a peptide of virtually any amino acid sequence or any molecule or atoms capable of connecting the RAP, RAP fragment or RAP variant to the active agent.

In some embodiments, the linker comprises a chain of atoms from 1 to about 60, or 1 to 30 atoms or longer, 2 to 5 atoms, 2 to 10 atoms, 5 to 10 atoms, or 10 to 20 atoms long In some embodiments, the chain atoms are all carbon atoms. In some embodiments, the chain atoms are selected from the group consisting of C, O, N, and S. Chain atoms and linkers may be selected according to their expected solubility (hydrophilicity) so as to provide a more soluble conjugate. In some embodiments, the linker provides a functional group that is subject to enzymatic attack in a lysosome. In some embodiments, the linker provides a functional group which is subject to attack by an enzyme found in the target tissue or organ and which upon attack or hydrolysis severs the link between the active agent and the RAP, RAP fragment or RAP variant. In some embodiments, the linker provides a functional group that is subject to hydrolysis under the conditions found at the target site (e.g., low pH of a lysosome). A linker may contain one or more such functional groups. In some embodiments, the length of the linker is long enough to reduce the potential for steric hindrance (when an active agent is large) between one or both of the RAP, RAP fragment or RAP variant binding site and the active agent active binding site.

If the linker is a covalent bond or a peptide and the active agent is a polypeptide, the entire conjugate can be a fusion protein. Such peptidyl linkers may be any length. Exemplary linkers are from about 1 to 50 amino acids in length, 5 to 50, or 10 to 30 amino acids in length. Such fusion proteins may be produced by recombinant genetic engineering methods known to one of ordinary skill in the art. In some embodiments, the RAP, RAP fragment or RAP variant portion of the conjugate is formulated to rapidly degrade to release the active compound. In other embodiments, the linker is subject to cleavage under intracellular, or more preferably, lysosomal environmental conditions to release or separate the active agent portion from the RAP, RAP fragment or RAP variant polypeptide portion.

The conjugate can comprise one or more active agents linked to the same RAP, RAP fragment or RAP variant. For example, conjugation reactions may conjugate from 1 to 5, about 5, about 1 to 10, about 5 to 10, about 10 to 20, about 20 to 30, or 30 or more molecules of an active agent to the RAP, RAP fragment or RAP variant polypeptide. These formulations can be employed as mixtures, or they may be purified into specific stoichiometric formulations. Those skilled in the art are able to determine which format and which stoichiometric ratio is preferred. Further, more than one type of active agent may be linked to the RAP, RAP fragment or RAP variant polypeptide where delivery of more than one type of an agent to a target site or compartment is desired. A plurality of active agent species may be attached to the same RAP, RAP fragment or RAP variant polypeptide e.g., adriamycin-cis-platinum RAP, (or other RAP variant) conjugates. Thus, the conjugates may consist of a range of stoichiometric ratios and incorporate more than one type of active agent. These, too, may be separated into purified mixtures or they may be employed in aggregate.

The RAP, RAP fragment or RAP variant or fragments thereof, conjugated a described herein and using methods known in the art, may be modified as desired to enhance its stability or pharmacokinetic properties (e.g., PEGylation). Suitable linkers and their functional groups for conjugating RAP variant polypeptides and an active agent, and the synthetic chemical methods readily adaptable for preparing such, are described in U.S. Patent Publication No. 2003253890, herein incorporated by reference in its entirety.

The synthesis of these conjugates is efficient and convenient, producing high yields and drugs with enhanced aqueous solubility.

F. ACTIVE AGENTS

Active agents according to the invention include agents that can affect a biological process. Particularly preferred active agents for use in the compounds compositions and methods of the invention are therapeutic agents, including drugs and diagnostic agents. The term "drug" or "therapeutic agent" refers to an active agent that has a pharmacological activity or benefits health when administered in a therapeutically effective amount. Particularly preferred agents are naturally occurring biological agents (e.g., enzymes, proteins, polynucleotides, antibodies, polypeptides, nanoparticles, glyconjugates). In some embodiments, the active agent conjugated to a RAP, RAP fragment or RAP variant is a molecule, as well as any binding portion or fragment thereof, that is capable of modulating a biological process in a living host. Examples of drugs or therapeutic agents include substances that are used in the prevention, diagnosis, alleviation, treatment or cure of a disease or condition. It is particularly contemplated that the agent is not an agent that causes a disease.

i. Protein Active Agents

The active agent can be a non-protein or a protein. The active agent can be a protein or enzyme or any fragment of such that still retains some, substantially all, or all of the therapeutic or biological activity of the protein or enzyme. In some embodiments, the protein or enzyme is one that, if not expressed or produced or if substantially reduced in expression or production, would give rise to a disease. Preferably, the protein or enzyme is derived or obtained from a human or mouse.

In preferred embodiments of the invention, when the active agent conjugated to RAP, RAP fragment or RAP variant polypeptide is a protein or enzyme, or fragment thereof possessing a biological activity of the protein or enzyme, the active agent has an amino acid sequence identical to the amino acid sequence to the corresponding portion of the human or mammalian protein or enzyme. In other embodiments, the active agent moiety of the conjugate is a protein or enzyme native to the species of the human or mammal. In other embodiments, the protein or enzyme, or fragment thereof, is substantially homologous (i.e., at least 80%, 85%, 90%, 95%, more preferably 98%, or most preferably 99% identical in amino acid sequence over a length of at least 10, 25, 50, 100, 150, or 200 amino acids, or the entire length of the active agent) to a native sequence of the corresponding human or mammal protein or enzyme.

The RAP, RAP fragment or RAP variant-active agent conjugate can comprise one or more active agent moieties (e.g., 1 to 10 or 1 to 4 or 2 to 3 moieties) linked to the RAP, RAP fragment or RAP variant or LRP1-binding fragment thereof. For example, conjugation reactions may conjugate from 1 to 4 or more molecules to a single RAP, RAP fragment or RAP variant. These formulations can be employed as mixtures, or they may be purified into specific RAP, RAP fragment or RAP variant polypeptide-agent stoichiometric formulations. Those skilled in the art are able to determine which format and which stoichiometric ratio is preferred.

These RAP, RAP fragment or RAP variant conjugated agents may consist of a range of stoichiometric ratios. These, too, may be separated into purified mixtures or they may be employed in aggregate. It may be the order of RAP, RAP fragment or RAP variant and the active agent in the fusion is important for the ability of the LRP1 binding moiety to bind to LRP1. Therefore, in preferred embodiments, the RAP, RAP fragment or RAP variant is located N-terminally to the protein active agent coding sequence.

ii. Drug Active Agents

Generally, the drug active agent may be of any size. Preferred drugs are small organic molecules that are capable of binding to the target of interest. A drug moiety of the conjugate, when a small molecule, generally has a molecular weight of at least about 50 D, usually at least about 100 D, where the molecular weight may be as high as 500 D or higher, but will usually not exceed about 2000 D.

The drug moiety is capable of interacting with a target in the host into which the conjugate is administered during practice of the subject methods.

In some embodiments, the active agent or drug has a hydroxyl or an amino group for reacting with the isocyanate reagent or the active agent is chemically modified to introduce a hydroxyl or an amino group for reacting with the isocyanate reagent.

In some embodiments, the active agent or drug comprises a region that may be modified and/or participate in covalent linkage, preferably, without loss of the desired biological activity of the active agent. The drug moieties often comprise cyclical carbon or heterocyclic structures and/or aromatic or polyaromatic structures substituted with one or more of the above functional groups. Also of interest as drug moieties are structures found among biomolecules, proteins, enzymes, polysaccharides, and polynucleic acids, including peptides, saccharides, fatty acids, steroids, purines, pyrimidines, derivatives, structural analogs or combinations thereof.

Suitable active agents include, but are not limited to, psychopharmacological agents, such as (1) central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g., central antitussives (opium alkaloids and their derivatives); pharmacodynamic agents, such as (1) peripheral nervous system drugs, e.g., local anesthetics (ester derivatives, amide derivatives), (2) drugs acting at synaptic or neuroeffector junctional sites, e.g., cholinergic agents, cholinergic blocking agents, neuromuscular blocking agents, adrenergic agents, antiadrenergic agents, (3) smooth muscle active drugs, e.g., spasmolytics (anticholinergics, musculotropic spasmolytics), vasodilators, smooth muscle stimulants, (4) histamines and antihistamines, e.g., histamine and derivative thereof (betazole), antihistamines (H1-antagonists, H2-antagonists), histamine metabolism drugs, (5) cardiovascular drugs, e.g., cardiotonics (plant extracts, butenolides, pentadienolids, alkaloids from erythrophleum species, ionophores, adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g., antianemia drugs, blood coagulation drugs (hemostatics, anticoagulants, antithrombotics, thrombolytics, blood proteins and their fractions), (7) gastrointestinal tract drugs, e.g., digestants (stomachics, choleretics), antiulcer drugs, antidiarrheal agents, (8) locally acting drugs; chemotherapeutic agents, such as (1) anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e., antineoplastic agents or cytotoxic drugs, such as alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) Dacarbazine and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g., Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (Vepesid, VP-16-213), Amsarcrine (AMSA, m-AMSA), Mitotane (Lysodren), Mitoxantrone (Novatrone), (9) receptor tyrosine kinase inhibitors, which may inhibit such kinases as FGFR, PDGFR, VEGFR2, VEGFR, HER2, Ebr-B2 and others, including but not limited to, SU6668 (FGFR, PDGFR, VEGFR, VEGFR2) Sunitinib (PDGFR), Bevacizumab (VEGFR), Gefitinib, Erlotinib, Cetuximab (EGFR), Lapatinib (Erb-B2), Trastuzumab (HER2) and Alemtuzumab (anti-CD52), Dasatinib, Imatinib, Sorafenib, Sunitinib, and the like, (10) anti-neoplastic agents, including but not limited to, SU6668, Bevacizuma, Sunitinib, Vandetanib (VEGFR2), BMS-275291, COL-3, Neovastat (MMPs), vitaxin, and the like. Preferred chemotherapeutic agents are those, which in the free form, demonstrate unacceptable systemic toxicity at desired doses. The general systemic toxicity associated with therapeutic levels of such agents may be reduced by their linkage to the RAP, RAP fragment or RAP variant polypeptide. Particularly preferred are cardiotoxic compounds that are useful therapeutics but are dose limited by cardiotoxicity. A classic example is adriamycin (also known as doxorubicin) and its analogs, such as daunorubicin. Linking RAP, RAP fragment or a RAP variant polypeptide to such drugs may prevent accumulation of the active agent at the heart and associated cardiotoxicity.

Suitable active agents include, but are not limited to: Antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; beta.-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g., apicycline, chlortetracycline, clomocycline, etc.; synthetic antibacterial agents, such as 2,4-diaminopyrimidines, nitrofurans, quinolones and analogs thereof, sulfonamides, sulfones;

Suitable active agents include, but are not limited to: Antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, etc., thiocarbamates, e.g., tolciclate, triazoles, e.g., fluconazole, itraconazole, terconazole;

Suitable active agents include, but are not limited to: Antihelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

Suitable active agents include, but are not limited to: Antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

Suitable active agents include, but are not limited to: Antiprotozoan agents, such as: acranil, timidazole, ipronidazole, ethylstibamine, pentamidine, acetarsone, aminitrozole, anisomycin, nifuratel, timidazole, benzidazole, suramin, and the like.

Suitable drugs for use as active agents are also listed in: Goodman and Gilman's, The Pharmacological Basis of Therapeutics (9th Ed) (Goodman et al. eds) (McGraw-Hill) (1996); and 1999 Physician's Desk Reference (1998).

Suitable active agents include, but are not limited to: antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,996, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 4,684,747, 4,618,685, 4,611,066, 4,550,187, 4,550,186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psychopharmacological/psychotropic agents, as disclosed in U.S. Pat. Nos. 5,192,799, 5,036,070, 4,778,800, 4,753,951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620, 5,665,752, 5,656,661, 5,635,516, 5,631,283, 5,622,948, 5,618,835, 5,607,959, 5,593,980, 5,593,960, 5,580,888, 5,552,424, 5,552,422, 5,516,764, 5,510,361, 5,508,026, 5,500,417, 5,498,405, 5,494,927, 5,476,876, 5,472,973, 5,470,885, 5,470,842, 5,464,856, 5,464,849, 5,462,952, 5,459,151, 5,451,686, 5,444,043, 5,436,265, 5,432,181, RE034,918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 5,006,542, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

immunomodulatory agents, as disclosed in U.S. Pat. Nos. 4,446,128, 4,524,147, 4,720,484, 4,722,899, 4,748,018, 4,877,619, 4,998,931, 5,049,387, 5,118,509, 5,152,980, 5,256,416, 5,468,729, 5,583,139, 5,604,234, 5,612,060, 5,612,350, 5,658,564, 5,672,605, 5,681,571, 5,708,002, 5,723,718, 5,736,143, 5,744,495, 5,753,687, 5,770,201, 5,869,057, 5,891,653, 5,939,455, 5,948,407, 6,006,752, 6,024,957, 6,030,624, 6,037,372, 6,037,373, 6,043,247, 6,060,049, 6,087,096, 6,096,315, 6,099,838, 6,103,235, 6,124,495, 6,153,203, 6,169,087, 6,255,278, 6,262,044, 6,290,950, 6,306,651, 6,322,796, 6,329,153, 6,344,476, 6,352,698, 6,365,163, 6,379,668, 6,391,303, 6,395,767, 6,403,555, 6,410,556, 6,412,492, 6,468,537, 6,489,330, 6,521,232, 6,525,035, 6,525,242, 6,558,663, 6,572,860;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514, 4,147,872, 4,133,819, 4,124,713, 4,117,012, 4,064,272, 4,022,836, 3,966,944;

cholinergic agents, as disclosed in U.S. Pat. Nos. 5,219, 872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091,528, 5,091,528, 4,835,157, 5,708,015, 5,594,027, 5,580,892, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874, 479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102; the disclosures of all the above of which are herein incorporated by reference.

The drug moiety of the conjugate may be the whole drug or a binding fragment or portion thereof that retains its affinity and specificity for the target of interest while having a linkage site for covalent bonding to the vector protein ligand or linker. The conjugates of such drugs may be used for the same disorders, diseases, and indications as the drugs themselves.

G. CANCER CHEMOTHERAPEUTIC ACTIVE AGENTS

Preferred cancer chemotherapeutic agents for use in the RAP, RAP fragment or RAP variant based conjugates useful in the methods of the invention include all drugs which may be useful for treating liver tumors or other neoplasia in or around the liver, either in the free form, or, if not so useful for such tumors in the free form, useful when linked to the RAP, RAP fragment or RAP variant or LRP1-binding fragment thereof. Such chemotherapeutic agents are preferably cytotoxic chemotherapeutic agents including but not limited to adriamycin (also known as doxorubicin), cisplatin, paclitaxel, analogs thereof, and other chemotherapeutic agents demonstrate activity against tumors ex vivo and in vivo. Such chemotherapeutic agents also include alkylating agents, antimetabolites, natural products (such as vinca alkaloids, epidophyllotoxins, antibiotics, enzymes and biological response modifiers), topoisomerase inhibitors, microtubule inhibitors, spindle poisons, hormones and antagonists, and miscellaneous agents such as platinum coordination complexes, anthracendiones, substituted ureas, etc. Those of skill in the art will know of other chemotherapeutic agents.

Cytotoxic chemotherapeutic agents useful in treating cancers or neoplasias, including, but not limited to, radioisotopes such as $^{131}$I (Iodine), $^{125}$I, $^{111}$In (indium), $^{90}$Y (Yttrium), $^{67}$Cu (Copper), $^{127}$Lu (Lutetium), $^{212}$Bi (Bismuth), $^{213}$Bi, $^{255}$Fm (Fermium), $^{149}$Tb (Terbium), $^{223}$Rd (Radium), $^{213}$Pb (lead), $^{212}$Pb, $^{211}$At (Astatine), $^{89}$Sr (Strontium), $^{153}$Sm (Samarium), $^{166}$Ho (Holmium), $^{225}$Ac (Actinium), $^{186}$Re (Rhenium), $^{67}$Ga (Gallium), $^{68}$Ga and $^{99m}$Tc (Technetium), may be conjugated a RAP, RAP fragment or RAP variant useful in the invention. The radioisotopes may be linked to the polypeptide using metal chelating agents common in the art for such purposes, including, but not limited to 1,4,7,10-tetraazacyclo-11 dodecane-N,N',N",N'"-tetraacetic acid (DOTA), 1,4,8,11-tetraazacyclotetradecane N,N',N",N'"-tetraacetic acid (TETA), diethylene triamine penta-acetate (DTPA), dimercaptosuccinic acid (DMSA), tetraazacyclotridecane-N,N',N",N'"-tetraacetic acid (TRITA), and 1,5,9, 13-tetraazacyclohexadecane-N,N',N",N'"-tetraacetic acid (HETA), hydroxyethylidene diphosphonate (HEDP), HEXA, and ethylenediaminetetraacetic acid (EDTA), which allow "loading" of the radioisotopes onto the polypeptide.

Preferred chemotherapeutic agents are those, which in the free form, demonstrate unacceptable systemic toxicity at desired doses. The general systemic toxicity associated with therapeutic levels of such agents is reduced by their linkage to a RAP, RAP fragment or RAP variant. Particularly preferred are cardiotoxic compounds that are useful therapeutics but are dose limited by cardiotoxicity. A classic example is adriamycin (also known as doxorubicin) and its analogs, such as daunorubicin. Linking a RAP, RAP fragment or RAP variant to such drugs decreases accumulation and associated cardiotoxicity at the heart.

H. NANOPARTICLES

Nanoparticles are macromolecular assemblies constructed from biodegradable and non-biodegradable polymers or from other materials such as lipids. Such assemblies may be engineered to contain therapeutic molecules in cavities within the particle. Through this means, nanoparticles provide a means of altering the biodistribution, pharmacokinetics, immunogenicity and potency of drugs. Attachment of suitable RAP, RAP fragment or RAP variants would, in turn, provide a means of increasing the specificity of tissue distribution of these molecules.

I. METHODS OF PRODUCING RAP CONJUGATES i. Host Cells

Host cells used to produce chimeric proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types. Host cells can include mutants of CHO cells that do not express LRP such as CHO13-5-1 (FitzGerald et al., J. Biol. Chem., 129(6):1533-41, 1995).

Cells that contain and express DNA or RNA encoding the chimeric protein are referred to herein as genetically modified cells. Mammalian cells that contain and express DNA or RNA encoding the chimeric protein are referred to as genetically modified mammalian cells. Introduction of the DNA or RNA into cells is by a known transfection method, such as electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the DNA or RNA can be introduced by infection with a viral vector. Methods of producing cells, including mammalian cells, which express DNA or RNA encoding a chimeric protein are described in U.S. Pat. Nos. 6,048,729, 5,994,129, and 6,063,630. The teachings of each of these applications are expressly incorporated herein by reference in their entirety.

ii. Nucleic Acid Constructs

A nucleic acid construct used to express the chimeric protein can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to chimeric protein-encoding sequences, sequences sufficient for expression of the protein in the cells and, optionally, for replication of the construct. It typically includes a promoter, chimeric protein-encoding DNA and a polyadenylation site. The DNA encoding the chimeric protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it need include only the chimeric protein-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

iii. Cell Culture Methods

Mammalian cells containing the chimeric protein-encoding DNA or RNA are cultured under conditions appropriate for growth of the cells and expression of the DNA or RNA. Those cells which express the chimeric protein can be identified, using known methods and methods described herein, and the chimeric protein isolated and purified, using known methods and methods also described herein; either with or without amplification of chimeric protein production. Identification can be carried out, for example, through screening genetically modified mammalian cells displaying a phenotype indicative of the presence of DNA or RNA encoding the chimeric protein, such as PCR screening, screening by Southern blot analysis, or screening for the expression of the chimeric protein. Selection of cells having incorporated chimeric protein-encoding DNA may be accomplished by including a selectable marker in the DNA construct and culturing transfected or infected cells containing a selectable marker gene under conditions appropriate for survival of only those cells that express the selectable marker gene. Further amplification of the introduced DNA construct can be affected by culturing genetically modified mammalian cells under conditions appropriate for amplification (e.g., culturing genetically modified mammalian cells containing an amplifiable marker gene in the presence of a concentration of a drug at which only cells containing multiple copies of the amplifiable marker gene can survive).

Genetically modified mammalian cells expressing the chimeric protein can be identified, as described herein, by detection of the expression product. For example, mammalian cells expressing chimeric protein in which the carrier is a RAP, RAP fragment or RAP variant can be identified by a sandwich enzyme immunoassay. The antibodies can be directed toward the LRP1-binding portion or the active agent portion of the conjugate.

iv. Production of RAP Fragment or RAP Variant Polypeptides

RAP fragment or RAP variant polypeptides for use according to the invention include those disclosed in U.S. Pat. No. 5,474,766 and International Patent Application No. PCT/US2006/36453 that is incorporated herein by reference in its entirety for the purposes of disclosing such peptides and their production for use in the compounds and compositions of the present invention. RAP fragment and RAP variant polypeptides are produced using any of protein preparation and purification methods known to those of skill in the art.

The ligand is purified from a naturally occurring source of the protein, can be isolated from a recombinant host expressing the ligand, or synthesized using well known techniques in protein synthesis. A skilled artisan readily adapts a variety of such techniques in order to obtain a RAP fragment or RAP variant that contain the receptor-binding site. (Melman et al., J. Biol. Chem. 276 (31): 29338-29346 (2001); Savonen et al., J Biol. Chem. 274(36): 25877-25882 (1999); Nielsen et al. Proc. Natl. Acad. Sci. USA 94:7521-7525 (1997); Medved et al., J. Biol. Chem. 274(2): 717-727 (1999); Rall et al., J. Biol. Chem. 273(37): 24152-24157 (1998); Orlando et al., Proc. Natl. Acad. Sci. USA 3161-3163 (1994)).

The isolation of native RAP proteins has been previously described (Ashcom et al., J. Cell. Biol. 110:1041-1048 (1990) and Jensen et al., FEBS Lett. 255:275-280 (1989)). RAP variants and fragments are generated from isolated native protein which are converted by enzymatic and/or chemical cleavage to generate fragments of the whole protein. U.S. Pat. No. 6,447,775 is herein incorporated by reference with particular reference to such methods for obtaining RAP variant polypeptides. In addition, the RAP fragment or RAP variant are expressed in a recombinant bacteria (Williams et al., J. Biol. Chem. 267:9035-9040 (1992); Wurshawsky et al., J. Biol. Chem. 269:3325-3330 (1994)). Procedures for purifying the 39 kDa RAP protein from a recombinant E. coli strain have been previously described (Herz et al., J. Biol. Chem. 266, 21232-21238 (1991); U.S. Pat. No. 5,474,766).

Cultures of E. coli strain DH5alpha carrying the expression plasmid pGEX-39 kDa are grown to mid-log phase in LB medium with 100 µg/ml ampicillin at 37° C. Cultures are cooled to 30° C. and supplemented with 0.01% isopropylthio-beta-D-galactoside to induce expression of the glutathione-S-transferase-39 kDa fusion protein. Following a 4-6 hour induction at 30° C., cultures are cooled with ice and recovered by centrifugation. Further steps are conducted at 4° C. Cell pellets are lysed in PBS with 1% Triton X-100, 1 µM pepstatin, 2.5 µg/ml leupeptin, 0.2 mM phenylmethylsulfonyl fluoride (PMSF), and 1 µM ethylenediaminetetraacetate (EDTA). The lysate is sonicated with a Branson Model 450 Sonifier and the resulting membranes and other cellular debris are separated by centrifugation at 15,000 g for 15 minutes. The recovered supernatant is incubated overnight with agarose immobilized glutathione beads (Sigma Chemical Co.) in PBS and 0.1% sodium azide. The beads are washed, and the fusion protein eluted by competition with 5 mM reduced glutathione (Sigma Chemical Co.). Following dialysis, the fusion protein is cleaved by an overnight incubation with 100 ng of activated human thrombin per 50 µg of fusion protein. The glutathione-S-transferase epitope is subsequently be removed by further incubation with agarose immobilized glutathione beads.

While the above method is described for the production and purification of RAP, as indicated above, other RAP fragments or RAP variants also may be produced using similar techniques. A review of such ligands may be found in Christensen and Birn, (Am. J. Physiol. Renal Physiol., 280:F562-F573, 2001, see particularly Table 2 and references cited therein) Techniques for making and purifying such ligands are well known to those of skill in the art.

J. CHARACTERIZATION OF RAP CONJUGATES i. Labels

In some embodiments, the RAP, RAP fragment and RAP variant-based active agent conjugate is labeled to facilitate its detection. A "label" or a "detectable moiety" is a composition detectable by spectroscopic, photochemical, biochemical, immunochemical, chemical, or other physical means. For example, labels suitable for use in the present invention include, for example, radioactive labels (e.g., $^{32}P$), fluorophores (e.g., fluorescein), electron dense reagents, enzymes (e.g., as commonly used in an ELISA), biotin, digoxigenin, or haptens and proteins which can be made detectable, e.g., by incorporating a radiolabel into the hapten or peptide, or used to detect antibodies specifically reactive with the hapten or peptide.

As noted above, depending on the screening assay employed, the active agent, the linker or the RAP, RAP fragment or RAP variant polypeptide portion of a conjugate may be labeled. The particular label or detectable group used is not a critical aspect of the invention, as long as it does not significantly interfere with the biological activity of the conjugate. The detectable group can be any material having a detectable physical or chemical property. Thus, a label is any composition detectable by spectroscopic, photochemical, biochemical, immunochemical, electrical, optical or chemical means.

Examples of labels suitable for use in the present invention include, but are not limited to, fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugating an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand binds to another molecules (e.g., streptavidin) molecule, which is either inherently detectable or covalently bound to a signal system, such as a detectable enzyme, a fluorescent compound, or a chemiluminescent compound.

The conjugates can also be conjugated directly to signal generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands may be used in the diagnosis of a disease or health condition.

K. METHODS OF USING, PHARMACEUTICAL COMPOSITIONS, AND THEIR ADMINISTRATION

The conjugates can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The conjugates can be utilized in aerosol formulation to be administered via inhalation. The compounds of the present invention can be formulated into pressurized acceptable propellants such as dichlorodifluoromethane, propane, nitrogen and the like.

Unit dosage forms for injection or intravenous administration may comprise the conjugate in a composition as a solution in sterile water, normal saline or another pharmaceutically acceptable carrier.

In practical use, the RAP, RAP fragment or RAP variant conjugate, described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

With respect to transdermal routes of administration, methods for transdermal administration of drugs are disclosed in Remington's Pharmaceutical Sciences, 17th Edition, (Gennaro et al. Eds. Mack Publishing Co., 1985). Dermal or skin patches are a preferred means for transdermal delivery of the conjugates useful in the methods of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

Those of skill will readily appreciate that dose levels can vary as a function of the specific compound, the severity of the symptoms and the susceptibility of the subject to side effects. Preferred dosages for a given compound are readily determinable by those of skill in the art by a variety of means, including, but not limited to dose response and pharmacokinetic assessments conducted in patients, test animals, and in vitro.

In each of these aspects, the compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The compositions may be conveniently presented in unit dosage form and prepared by any of the methods well-known in the art of pharmacy.

Compositions of the present invention may be administered encapsulated in or attached to viral envelopes or vesicles, or incorporated into cells. Vesicles are micellular particles which are usually spherical and which are frequently lipidic. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer compounds intracellularly and to deliver compounds to the target organs. Controlled release of a p97-composition of interest may also be achieved using encapsulation (see, e.g., U.S. Pat. No. 5,186,941).

Any route of administration that delivers the RAP-, RAP fragment- or RAP variant-based active agent conjugate into the blood stream may be used. Preferably, the composition is administered peripherally, most preferably intravenously or by cardiac catheter. Intrajugular and intracarotid injections are also useful. Compositions may be administered locally or regionally, such as intraperitoneally or subcutaneously on intramuscularly. In one aspect, compositions are administered with a suitable pharmaceutical diluent or carrier.

Dosages to be administered will depend on individual needs, on the desired effect, the active agent used, the biopolymer and on the chosen route of administration. Preferred dosages of a conjugate range from about 0.2 pmol/kg to about 25 nmol/kg, and particularly preferred dosages range from 2-250 pmol/kg; alternatively, preferred doses of the conjugate may be in the range of 0.02 to 2000 mg/kg. These dosages will be influenced by the number of active agent or drug moieties associated with the biopolymer. Alternatively, dosages may be calculated based on the active agent administered.

In preferred embodiments the conjugate comprises a RAP variant. For instance, doses of RAP, RAP fragment or RAP variant-adriamycin comprising from 0.005 to 100 mg/kg of adriamycin are also useful in vivo. Particularly preferred is a dosage of RAP, RAP fragment or RAP variant-adriamycin comprising from 0.05 mg/kg to 20 mg/kg of adriamycin. Those skilled in the art can determine suitable doses for compounds linked to a RAP variant based in part on the recommended dosage used for the free form of the compound. Conjugation of the active agent to a RAP variant generally reduces the amount of drug needed to obtain the same effect.

The conjugates and modulators of the invention are useful for therapeutic, prophylactic and diagnostic intervention in animals, and in particular in humans. RAP, RAP fragment or RAP variant compounds may show preferential accumulation in particular tissues. Preferred medical indications for diagnostic uses include, for example, any condition associated with a target organ of interest (e.g., lung, liver, kidney, spleen).

The subject methods find use in the treatment of a variety of different disease conditions. In certain embodiments, of particular interest is the use of the subject methods in disease conditions where an active agent or drug having desired activity has been previously identified, but in which the active agent or drug is not adequately delivered to the target site, area or compartment to produce a fully satisfactory therapeutic result. With such active agents or drugs, the subject methods of conjugating the active agent to a RAP, RAP fragment or RAP variant can be used to enhance the therapeutic efficacy and therapeutic index of active agent or drug.

The specific disease conditions treatable by with the subject conjugates are as varied as the types of drug moieties that can be present in the conjugate. Thus, disease conditions which affect the liver and treatable by the methods of the invention include cellular proliferative diseases, such as neoplastic diseases, autoimmune diseases, hormonal abnormality diseases, degenerative diseases, diseases of aging, and the like.

Treatment is meant to encompass any beneficial outcome to a subject associated with administration of a conjugate including a reduced likelihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

L. DELIVERY OF RAP CONJUGATES TO THE LIVER

The majority of the liver is perfused primarily by the portal vein. Reliance of tumor on arterial blood, coupled with the efficiency of first-pass capture, should allow sparing of a significant portion of non-cancerous liver tissue after intravenous administration of RAP-conjugated chemotherapeutics.

In addition to the potential advantages afforded by the liver vasculature, the relative expression levels of LRP1 on HCC tumor cells and surrounding tissue may further favor the efficacy of RAP conjugates. Studies have demonstrated at least ten-fold enhancement of LRP1 expression on hepatocytes following neoplastic transformation (23). In marked contrast, others have shown that LRP1 is significantly underexpressed in non-cancerous, but cirrhotic, liver tissue (24). Enhanced LRP1 expression on tumor cells, with diminished expression elsewhere in the diseased liver, should, like arterial delivery with first-pass capture, result in non-uniform delivery of RAP conjugates, with a preference for tumor tissue. Non-uniform delivery, along with the generally enhanced sensitivity of rapidly proliferating tumor cells to chemotherapeutic agents, may circumvent the barrier to treatment presented by diminished liver reserve in the majority of HCC patients.

An effective method of treating hepatocellular carcinomas is administration of Yttrium-90 ($^{90}$Y). $^{90}$Y is a cancer chemotherapeutic with high antibiotic efficacy against a wide variety tumors. $^{90}$Y decay produces a high-energy beta particle, making it a particularly good choice for large solid tumors like those common in HCC. Yttrium becomes the stable element zirconium upon decay. Delivery of $^{90}$Y to hepatocellular tumors is currently achieved with the use of nuclide-containing insoluble glass beads (THERASPHERE™) administered by transarterial catheterization. This method is effective to treatment of large, well-defined tumors, but is less useful for cases involving multiple, small tumors or in cases involving metastasis. Another approach would be to conjugate $^{90}$Y or other chemotherapeutics to agents that target tumor cells selectively. An example of this approach can be found in the non-Hodgkin's lymphoma therapeutic ZEVALIN® (Ibritumomab tiuxetan), an anti-CD-22 monoclonal antibody with a metal chelator that is loaded with $^{90}$Y prior to injection.

RAP demonstrates a rapid diffusion to the liver after administration. Following intravenous bolus injection of 30 picomoles of protein, over 70% of exogenous RAP accumulates in the liver within 10 minutes (20). The circulating half-life of injected RAP is less than a minute. These pharmacokinetics are also observed at intravenous injections up to 2.5 mg/kg (60 nmol/kg) in rats (20). Similar pharmacokinetics have been reported for another high-affinity LRP1 ligand, protease-activated $\alpha$-2-macroglobulin, a 725 kD tetrameric serum glycoprotein (21). Only a small amount of RAP (<1% of injected dose) accumulates in heart, brain, muscle or kidney, indicating that both tissue and vascular expression of RAP-binding LDLR in these tissues is negligible for this application. Intravenously-administered RAP has shown no measurable toxicity in rodent and feline species. Capture efficiency of RAP by the liver is enhanced by an initial, low-affinity binding step to abundant cell-surface heparin sulfate proteoglycan on hepatocytes, with subsequent high-affinity binding and endocytosis by LRP1 (1,22). According to the invention, nearly quantitative delivery of RAP-, RAP fragment- or RAP variant-conjugated chemotherapeutics, such as $^{90}$Y, to liver after intravenous administration would significantly reduce the systemic toxicities associated with these drugs, reducing risk to the patient during treatment of HCC. RAP or RAP fragments or variants conjugated to $^{90}$Y or other active agents provides an effective method of delivery of active agents to the liver.

While a number of factors favor selective liver tumor targeting by RAP conjugates, it is also suggested that such agents will be effective on metastasized HCC. Metastasized tumor cells tend to retain their characteristics upon migration to heterotopic sites, demonstrating undiminished expression of LRP1 in extrahepatic metastasized human HCC (25). This factor may render metastasized HCC similarly susceptible to intravenously-administered conjugates of RAP, RAP fragment and RAP variant and appropriate chemotherapeutics or other active agents.

M. LIVER DISORDERS

One aspect of the invention contemplates conjugation of chemotherapeutic drugs or other agents to RAP, RAP fragment or RAP fragments or variants to deliver therapeutic compounds to the liver for the treatment of liver disease. Administration of a RAP conjugate to treat liver disease would address several problems associated with treatment of liver diseases, such as clearance of the agent by the liver, or drug resistance mechanisms in the plasma membrane (MDR, P-glycoprotein).

Liver diseases contemplated by the invention include, but are not limited to, those disorders discussed below. Hepatocellular carcinoma, or hepatoma, is the fifth most common cancer in the world and incidence rates have been climbing steadily. Tumorigenic hepatocytes retain high levels of LRP1 expression. Hepatocellular carcinoma does not respond well to chemotherapy because the tumor cells show high rates of drug resistance and because the chemotherapies used have serious toxicities, especially in the heart and kidney, due to systemic (intravenous) administration.

Hepatitis is a generic term for inflammation of the liver. Hepatitis can be acute or chronic and includes acute or chronic liver failure, e.g., due to virus (e.g., hepatitis A, B, C, D or E or non-ABODE, CMV, Epstein-Barr), fungal, rickettsial or parasitic infections, alcohol, chemical toxins, drugs (e.g. acetaminophen, amiodarone, isoniazid, halothane, chlorpromazine, erythromycin), metabolic liver disease (e.g., Wilson's disease, alpha1-antitrypsin deficiency), cancer, idiopathic autoimmune liver disease, cirrhosis (e.g. primary biliary cirrhosis), biliary obstruction. Infection of the liver by Hepatitis A, B and/or C virus can lead to slowly progressing liver disease leading to liver failure. Acute hepatitis infection is most commonly caused by hepatitis A. Both hepatitis B and hepatitis C infection can persist in the body and become longstanding infections (chronic). Hepatitis C can cause critical conditions including cirrhosis and cancer.

Additional liver disorders or conditions contemplated that are treatable using compositions conjugated to RAP or RAP fragments or variants include hepatic steatis (U.S. Pat. No. 6,596,762), cholestasis (U.S. Pat. No. 6,069,167), liver cirrhosis, toxic liver damage, post-hepatectomy conditions, and biliary obstruction.

Candidate drugs for conjugation to RAP or RAP fragments or variants for the treatment of liver disease include, but are not limited to: 5-fluorouracil, doxorubicin (adriamycin), mitomycin C, cisplatin, epirubicin, daunorubicin, etoposide, and other chemotherapeutic agents set out in Table 1, adefovir, lamivudine, entecavir, ribavirin, interferon alpha, pegylated interferon alpha-2a, interferon alpha-2b and other antivirals, Vitamin E, ursodeoxycholic acid, and other agents used to treat liver disorders.

TABLE 1

| Alkylating agents |
| --- |
| Nitrogen mustards | mechlorethamine
cyclophosphamide
ifosfamide
melphalan
chlorambucil

| Nitrosoureas |
| --- | carmustine (BCNU)
lomustine (CCNU)
semustine (methyl-CCNU)

| Ethylenimine/Methyl-melamine |
| --- | thriethylenemelamine (TEM)
triethylene thiophosphoramide
(thiotepa)
hexamethylmelamine
(HMM, altretamine)

| Alkyl sulfonates |
| --- | busulfan

| Triazines |
| --- | dacarbazine (DTIC)

| Antimetabolites |
| --- |

TABLE 1-continued

| Folic Acid analogs |
| --- | methotrexate
Trimetrexate
Pemetrexed
(Multi-targeted antifolate)

| Pyrimidine analogs |
| --- |

5-fluorouracil
fluorodeoxyuridine
gemcitabine
cytosine arabinoside
(AraC, cytarabine)
5-azacytidine
2,2'-difluorodeoxy-cytidine

| Purine analogs |
| --- |

6-mercaptopurine
6-thioguanine
azathioprine
2'-deoxycoformycin
(pentostatin)
erythrohydroxynonyl-adenine (EHNA)
fludarabine phosphate
2-chlorodeoxyadenosine
(cladribine, 2-CdA)

| Type I Topoisomerase Inhibitors |
| --- | camptothecin
topotecan
irinotecan

| Biological response modifiers |
| --- |

G-CSF
GM-CSF

| Differentiation Agents |
| --- | retinoic acid derivatives
Hormones and antagonists
Adrenocorticosteroids/antagonists prednisone and equivalents
dexamethasone
ainoglutethimide

| Progestins |
| --- | hydroxyprogesterone caproate
medroxyprogesterone acetate
megestrol acetate

| Estrogens |
| --- | diethylstilbestrol
ethynyl estradiol/equivalents

| Antiestrogen |
| --- | tamoxifen

| Androgens |
| --- | testosterone propionate
fluoxymesterone/equivalents

| Antiandrogens |
| --- | flutamide
gonadotropin-releasing
hormone analogs
leuprolide

| Nonsteroidal antiandrogens |
| --- | flutamide
Natural products
Antimitotic drugs

| Taxanes |
| --- | paclitaxel

| Vinca alkaloids |
| --- | vinblastine (VLB)
vincristine
vinorelbine
Taxotere ® (docetaxel)
estramustine

TABLE 1-continued estramustine phosphate
Epipodophylotoxins etoposide
teniposide
Antibiotics actimomycin D
daunomycin (rubido-mycin)
doxorubicin (adria-mycin)
mitoxantroneidarubicin
bleomycin
splicamycin (mithramycin)
mitomycinC
dactinomycin
aphidicolin
Enzymes L-asparaginase
L-arginase
Radiosensitizers metronidazole
misonidazole
desmethylmisonidazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinium coordination complexes cisplatin
Carboplatin
oxaliplatin
Anthracenedione
mitoxantrone
Substituted urea hydroxyurea
Methylhydrazine derivatives N-methylhydrazine (MIH)
procarbazine
Adrenocortical suppressant mitotane (o,p'-DDD)
ainoglutethimide
Cytokines interferon (α, β, γ)
interleukin-2
Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines
Radiation X-ray
ultraviolet light
gamma radiation
visible light
infrared radiation
microwave radiation Additional aspects and details of the invention will be apparent from the following examples, which are intended to be illustrative rather than limiting.

EXAMPLE 1

RAP Conjugate Delivers Toxin to Cells Through the LRP1 Pathway

In order to determine whether a RAP peptide conjugated to a cytotoxic agent could effectively deliver the toxin to the cell and initiate cell death, an in vitro assay was used to assess delivery of toxin via the RAP-LRP1 binding and internalization pathway.

Wild-type and LRP1-deficient CHO-K1 cells were grown in BioWhittaker Ultra-CHO supplemented with 5% fetal bovine serum. Cells were seeded in 12-well plates 48 hours prior to the experiment. A biotinylated, internally-disulfide linked, truncated peptide corresponding to a portion of RAP d3 (mini-RAPc, Hep1: biotin-GGSGGCGFREELKHFEAK-IEKHNHYQKQLEIAHEKLRHAESVGDGERVSRS REKHALLEGRTKELGYTVKKHLQDLSGGC) (SEQ ID NO: 9) was combined with equimolar amounts of a conjugate between streptavidin and the bacterial toxin saporin (ZAP, Advanced Targeting Systems, San Diego). The mixture was diluted into growth media to 100 nM and added to wells in duplicate. As controls, duplicate wells were incubated with RAP d3 peptide alone (mini-RAPc), the streptavidin-saporin conjugate alone (ZAP), both at 100 nM concentrations, and with saporin alone at 1 µM (SAP). Cells were incubated for 48 hours at 37° C., 5% $CO_2$ in a humidified chamber. Cell viability for each treatment condition was determined with an MTT assay kit (Invitrogen, San Diego).

Figure 2:
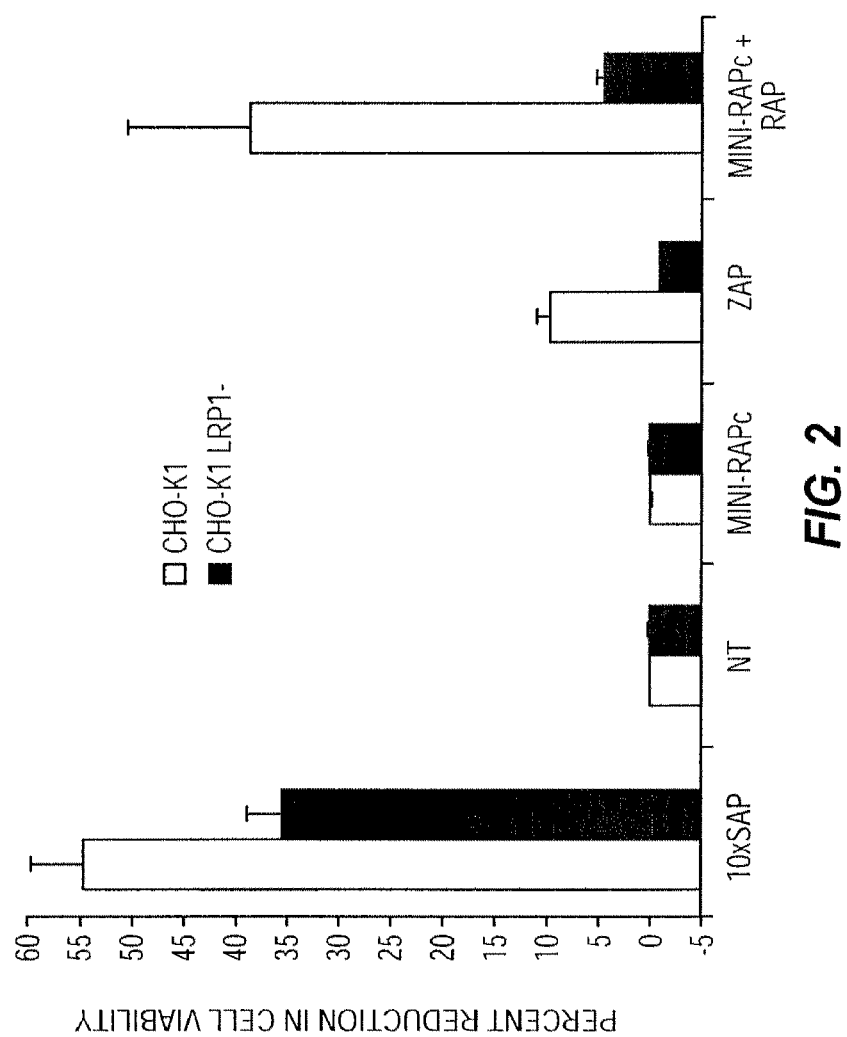
FIG. 2 shows the percent of cell death after administration of a RAP peptide-toxin conjugate to cells expressing the LRP1 receptor.

FIG. 2 shows that peptide alone had no significant effect on cell survival. The streptavidin-saporin conjugate alone reduced viable cell number by approximately 10% for wild-type CHO-K1, with no effect on LRP-deficient cells. The combination of peptide and cytotoxic conjugate reduced viable cell number by nearly 40% for wild-type CHO-K1, with only a 5% loss in LRP-deficient CHO-K1. Saporin alone (1 µM) resulted in losses of about 55% (wild-type) and 35% (LRP-deficient).

This data shows that the RAP d3 peptide can efficiently drive internalization of bound toxin through the LRP1 endocytic pathway, and provides a useful system for delivering compounds and therapeutics.

EXAMPLE 2

Administration of RAP and RAP Peptide Conjugates In Vivo

Infection with hepatitis B virus can produce a variety of outcomes ranging from asymptomatic infection, acute hepatitis, fulminant (rapid and severe onset) hepatitis, or development of a chronic low-level persistent infection. Between 5 and 10% of infected adults will become chronic carriers. Of those with chronic carrier status, 25-35% will eventually die from complications of the infection either from cirrhosis or hepatocellular carcinoma (HCC). The probability of developing hepatocellular carcinoma also increases with alcoholism, smoking and obesity. Prognosis for this disease is poor, with a reported 5-year median survival rate of under 5%.

HCC is the 5th most common malignant tumor to be diagnosed, and worldwide accounts for nearly 500,000 deaths annually. Surgical removal, transplant and physical destruction of tumor tissue are first choices for treatment, but only 5 to 10% of patients present with tumors suitable for these approaches (13-15). Further, systemic chemotherapy yields low response rates of 15-20%, both because of the toxicity of chemotherapeutics and tumor cell resistance (16-17).

For example, doxorubicin is a cancer chemotherapeutic with high efficiency against a wide variety of tumors, and is especially toxic to cells undergoing rapid growth, including tumor cells. However, the use of doxorubicin in the treatment of hepatocellular carcinoma is limited by significant liver and heart toxicity and suppression of blood-cell production (34). In addition, hepatocellular carcinoma cells show high rates of conversion to drug-resistant types (35).

An alternative approach to therapy utilizes radiation. For example, a new treatment for liver cancer that is currently being tested involves injecting microscopic glass beads that have been labeled with a radioactive material ($^{90}Y$) into the main liver artery, from where it passes in to the small blood vessels that perfuse tumor tissue. The radiation then destroys the tumor tissue. However, significant shunting of blood from the hepatic artery to the lungs precludes use of the glass beads in many patients. Significant reflux of beads into arteries feeding the gastrointestinal tract can also cause serious side-effects. Effective delivery of radiation therapy to tumor tissue therefore requires a more directed approach that does not rely on large materials that will be trapped in blood vessels.

A relevant animal model for hepatocellular carcinoma (HCC) for testing biodistribution and efficacy of therapeutics is the woodchuck hepatitis virus (WHV)-infected Eastern woodchuck (33). Nearly all woodchucks neonatally infected with the virus develop HCC within a median interval of 24 months. Median life expectancy is 30 months, however WHV-infected woodchucks do not develop cirrhosis, a condition present in the majority of HCC patients. Woodchuck hepatitis virus and human hepatitis B virus are similar in structure, genetics, methods of transmission, course of infection and progression to hepatocellular carcinoma. There are significant similarities that underscore the importance of this model. Similar to humans, more than half of all woodchucks exposed to hepatitis virus shortly after birth develop a chronic infection and nearly all chronically infected woodchucks develop hepatocellular carcinoma approximately 20 to 28 months after exposure. The remaining inoculated neonatal woodchucks often develop acute hepatitis, but will develop antibodies to the virus and recover. Between 17 and 25% of these "recovered" animals develop HCC between 29 to 56 months after exposure. Development of HCC after apparently recovering from hepatitis infection is also seen in humans.

To determine the effect of RAP and RAP peptides on delivery of agents to the liver, uptake and toxicity of control and RAP peptide conjugate therapeutics are studied in the woodchuck HCC model. Six chronically infected woodchucks and four uninfected woodchucks, approximately 1.5-2 years old are used.

As an initial test of pharmacokinetics, RAP peptide is conjugated to $^{90}Y$ (GE Healthcare) and administered intravenously to anaesthetized, HCC-bearing woodchucks. The RAP peptide contains a DOTA chelating moiety at the N-terminus to allow loading with radioisotopes such as $^{90}Y$. Modification of RAP peptide therefore allows the production of RAP peptide-$^{90}Y$ through incubation of the modified RAP peptide with Yttrium-90. A useful delivery compound will generally exhibit the following characteristics: 1) does not adversely affect the already compromised function of the liver, 2) measurable uptake by the liver and malignant liver tissue, 3) and upon uptake, is toxic to tumor cells and causes tumor regression.

As a control, additional tumor-bearing woodchucks are injected with equimolar amounts of free $^{90}Y$ or with bacterially-expressed full-length RAP containing at C-terminal cysteine conjugated to maleimido-DOTA to allow for production of RAP-$^{90}Y$.

$^{90}Y$ has well-defined toxicity and carcinogenicity profiles. It is expected that the pharmacokinetic profile of the RAP peptide-DOTA-$^{90}Y$ conjugate will not be significantly different from RAP, with rapid and near quantitative liver accumulation. RAP peptide pharmacokinetics are likely to be very similar in all mammalian species since LRP1 function, sequence and expression is strongly conserved within the sub-phylum. Similarly, RAP sequence is homologous among mammalian species, although the human sequence is identical only to that of other primates.

In order to determine a baseline level of comparison for the animals, the serum is analyzed for viral load and baseline levels of the following molecules: alkaline phosphatase (ALP)—an enzyme related to the bile ducts; often increased when they are blocked; aspartate aminotransferase (AST)—AST is a cytoplasmic enzyme in liver released from damaged cells, highest elevations occur in viral hepatitis and hepatotoxicity alanine aminotransferase (ALT). more specific for the liver than AST, but also present in kidney and muscle. Used to confirm that AST elevations are of liver origin (e.g., elevation of both AST and ALT strongly suggest hepatocellular injury; bilirubin, disproportionate elevation of conjugated bilirubin is seen in cholestasis and late in the course of chronic liver disease and serum bilirubin is increased in hepatocellular damage; albumin, measures the main protein made by the liver and tells whether or not the liver is making an adequate amount of this protein; gamma-glutamyl transferase (GGT), is an enzyme found in hepatic cells and highly sensitive to liver damage and repair; lactic acid dehydrogenase (LDH), found in liver cells, increases usually found upon cellular death and/or leakage from the cell due to injury; prothrombin time (PT), PT depends on the hepatic synthesis of the Vitamin-K-dependent factors: II, VII, IX and X, elevation in PT may be a sign of hepatic insufficiency, and total protein levels, to measure albumin and all other proteins in blood, including antibodies made to help fight off infections.

Once the basic status of the liver before treatment has been determined, the animals are anesthetized and both hind limbs are shaved and cleaned. The major (tarsal) vein in the leg is exposed and a catheter implanted into one leg. The woodchuck is then placed in a magnetic resonance imaging (MRI), 7T MRI. A scout image of the liver is acquired to determine the location and size of the liver. A multi-slice, multi-echo T2-weighted image gated to the mechanical ventilation of the woodchuck is acquired to give high quality images of the entire liver and the location of any tumors. A contrast agent (gadolinium) is injected through the catheter to improve the image quality of the T2 images and locate the tumor. The liver is also imaged using a 2D-CSI (two dimensional chemical shift imaging) phosphorus spectroscopy. Once the imaging is completed, the anaesthetized woodchucks are removed from the MRI and prepared for administration of the test agents.

In two infected woodchucks, RAP peptide-$^{90}Y$ is injected into the vein of the leg that does not have a catheter implanted in it. In a second pair of infected woodchucks, RAP-$^{90}Y$ is injected. The third pair of infected woodchucks will be injected with DOTA-$^{90}Y$. This condition serves as a negative control as the $^{90}Y$ will have no attached targeting moiety. The four control woodchucks will be injected with either RAP peptide-$^{90}Y$ or RAP-$^{90}Y$ dissolved in saline, to provide a comparison of the relative distribution of the two test compounds in animals with diseased and healthy livers.

Every five minutes starting from the time of drug injection, blood is collected from the contralateral catheter into separate sterile containers. Thirty minutes after the drug is injected, the woodchuck is euthanized and the whole carcass frozen. All blood samples collected during the experiment from all woodchucks are analyzed to determine the amount of $^{90}$Y-labeled drug circulating in the blood.

An STD10 (dose which results in severe toxicity in 10% of treated animals) determination of peptide is established followed by testing of one-tenth equivalent doses in non-rodents. Elevation of liver enzymes, along with histopathology, should provide a reliable measure of hepatotoxicity. Absence of severe toxicity in the non-rodent species allows direct calculation of a human starting dose for phase I studies at one tenth of the rat STD10 human-equivalent dose. Approximate effective dose calculations can be made based on previous data. An effective dose of 100 picomol/kg (3 nmol/m2) is derived by assuming a 500 MBq dose, quantitative loading of the RAP peptide-DOTA with $^{90}$Y and a specific activity for YCI3 of 74 petabecquerels per mole.

Primary delivery to of the RAP and RAP peptide and other compounds to the liver with some preference for HCC cells suggests an effective preferred delivery of the agent to the liver via RAP as compared to other tissue sites. Significant non-hepatic delivery or hepatic delivery with preference for normal tissue indicates the delivery route is not specific for the liver and HCC cells.

Further, administration of the RAP protein and RAP peptide and analysis of the pharmacokinetic profiles provide a method for determining that the RAP peptide and full-length RAP protein are both effective molecules to transport active agents to the liver, and that the RAP- and RAP peptide-conjugate mimics the LRP1-targeting behavior of full-length unconjugated RAP in vivo.

Thus, it is expected that both full-length RAP and shorter RAP fragments which mimic the full-length RAP LRP-1 specific binding are an effective means for delivering therapeutic compounds to the liver without inducing toxicity in healthy tissue.

EXAMPLE 3

Analysis of RAP Distribution after Administration In Vivo

In order to determine whether the RAP, RAP fragment or RAP variant is targeted more specifically to the liver than other tissue, localization and distribution of the RAP proteins and fragments conjugated to $^{90}$Y is performed. The animals are also monitored for localization and distribution of control drug and tumor cells.

To determine the relative levels of residual radioactivity in tissues of male woodchucks (*Marmota monax*) following a single dose of $^{90}$Y-labeled peptide or protein therapeutic agent, frozen sections of the treated animals are analyzed. Particular effort is made to distinguish tumor and non-tumor areas of the liver.

Tissue sections analyzed may include adipose tissue, gastrointestinal tract, skin, kidney, spinal cord, liver, spleen, adrenal gland, tumour tissue, non-tumour tissue, thymus, bone (vertebra), lung, thyroid/parathyroid gland, bone marrow, lymph node, brain, myocardium, pancreas, stomach wall, salivary gland (parotid), and small and large Intestine.

Immediately following sacrifice, each animal specimen is deep frozen in $CO_2$/hexane. Appropriate steps are taken to provide animal specimens suitable for cryosectioning which are then embedded in 2% carboxymethylcellulose (CMC) according to animal care protocols standard in the art. The specimen blocks are sectioned at 30 μm in a Leica CM-3600 cryomicrotome.

Sections are freeze-dried in the microtome cryocabinet for at least 16 hours or in the ThermoSavant freeze-dryer for approximately 30 minutes. Representatives of each section is exposed to a $^{14}$C-imaging plate for 30 minutes, 1, 2, 6, 12, 24, 48 and 72 hours (in a lead box and refrigerated at circa 4° C. to minimize background radiation artifacts), in order to provide the best resolution without loss of time. Following exposure, the imaging plates are read by the Fuji BAS-2500 scanner and its Fuji Image Reader software version 1.1.

It is expected that the RAP conjugates will preferentially be found in the liver of the subject animals, especially those having hepatocellular carcinoma or other liver damage.

EXAMPLE 4

Generation of Minimized RAP Peptides and Evaluation of Binding Affinity for LRP1

Additional minimized RAP peptides were generated as described herein.

Two additional peptides designated mRAP-8c and mRAP-14c were generated. mRAP-8c (SEQ ID NO: 10) comprises amino acid substitutions E246C, L247G at the N-terminal end of the fragment and substitutions L311G, S312C at the C-terminal end. mRAP-14c (SEQ ID NO: 11) comprises amino acid substitutions F250C and L308G, Q309C. The sequence biotin-GGSGG (SEQ ID NO: 12) was added N-terminally to each peptide.

The affinities of the mRAP-8c and MRAP-14c peptides for LRP1 cluster II were determined by solid phase binding assay. Briefly, recombinant human LRP1 cluster II (R&D Systems, amino acids 786-1165, with C-terminal Fc tag, 1 μg) was used to coat Nunc MAXISORP™ 96-well plates in TBS pH 8 supplemented with 5 mM $CaCl_2$ (TBSC) overnight at 4° C. Wells were washed with TBSC and blocked with TBSC containing 2% BSA.

In assays involving complexes between streptavidin and biotinylated peptide, LRP1 ligands were incubated with the immobilized receptor, in the presence or absence of inhibitors, for 2 hours in the above blocking buffer supplemented with 0.05% Tween-20 at room temperature. In assays involving complexes of the anti-biotin antibody and biotinylated peptide, all inhibitor solutions were preincubated with immobilized LRP1-C2 for one hour prior to direct addition of the RAP d3 ligand. Since the ligand binding competence of CR pairs requires calcium, identical binding reactions were done in the presence of 50 mM EDTA to provide a measure of non-specific binding. Control wells contained no added inhibitor. Wells were washed with TBS supplemented with 5 mM $CaCl_2$ and 0.05% Tween-20. Bound ligand was detected with either anti-5-peptide-HRP conjugate (Abcam) or anti-α-2-macroglobulin-HRP conjugate (Abcam). Excess HRP conjugate was removed and wells washed. Color was developed using TMB reagents (BioRad, Hercules, Calif.). Absorption at 450 nm was measured with a microplate spectrophotometer (Molecular Devices, Palo Alto).

Results of the binding assay showed that mRAP-8c exhibits affinity for LRP1 cluster II of approximately 4 nM, while mRAP-14c demonstrated an affinity of approximately 21 nM.

These results confirm that minimized RAP fragments, which may be approximately half the size of full-length RAP d3, efficiently bind the RAP receptor LRP1 and are useful to deliver agents to the liver via LRP1 endocytosis.

EXAMPLE 5

Evaluation of Cyclic RAP Peptide Oligomeric Combinations

Minimized RAP cyclic peptides retain similar affinity for appropriate CR pairs as isolated RAP d3, but do not exhibit the valency advantage conferred by full-length RAP binding to a receptor with many CR pairs. To reconstitute this valency advantage, multimeric assemblies of a biotinylated RAP d3 peptide on streptavidin or an anti-biotin antibody were generated (FIG. 3).

The truncated peptide (mRAPc), derived from RAP d3 and cyclized with an intramolecular disulfide bond, was used to test the effect of multimerization on binding to the second ligand binding domain of LRP1 (LRP1-C2). To simplify detection and allow multimerization of the peptide with streptavidin or an anti-biotin antibody, the peptide was fitted with an N-terminal biotin residue separated from the RAP sequence by a pentapeptide linker (GGSGG) (SEQ ID NO: 12). The monomeric mRAPc peptide was shown above to bind with high-affinity to LRP1-C2. Six of the seven CR pairs in LRP1-C2 share the necessary motif for RAP binding and have been demonstrated to bind independently to RAP d3 with similar affinities (1-5 nM) (Obermoeller et al., J Biol Chem 272:10761-10768, 1997; Andersen et al., J Biol Chem 275:21017-21024, 2000).

The ability of mRAPc, in the presence and absence of either streptavidin or anti-biotin antibody, to inhibit binding of recombinant RAP d3 to LRP1-C2 was measured by solid phase binding assay as described above.

Results show that the degree of inhibition (EC50) for the monomeric peptide was 29±7 nM (Table 3). The EC50 for mRAPc combined with one half mole equivalent of streptavidin, but under otherwise identical conditions, was 6±1 nM, a near 5-fold improvement over peptide alone. Mature RAP had an EC50 of 0.8±3 nM, 36-fold better than monomeric mRAPc peptide and still about 10-fold better than peptide assembled on streptavidin. The streptavidin alone had no inhibitory effect. The multifold enhancement of inhibition seen in the presence of streptavidin is consistent with an improvement in avidity upon multimerization of the minimized RAP domain.

TABLE 3

|  | mRAPc | mRAPc + streptavidin | RAP |
| --- | --- | --- | --- |
| $EC_{50}$ (2 nM RAP d3) | 29 ± 7 | 8 ± 2 | 0.8 ± 3 |
| Maximum binding | 0.34 | 0.26 | 0.29 |
| $r^2$ | 0.82 | 0.97 | 0.93 |
| relative to monomer | 1× | 3.6× | 36× |

Given the relatively weak monovalent affinity of the anti-biotin antibody for biotin (low nanomolar KD), it was hypothesized that preassembly of a multivalent complex consisting of two, suitably proximate, receptor-bound peptides and a single antibody would stabilize the peptide-antibody complex. Therefore, the antibody and peptide, in a molar ratio of one to three, was incubated with the immobilized receptor prior to washing and subsequent addition of the RAP d3 ligand. The same procedure was performed for the controls; peptide alone, antibody alone and full-length RAP. Using this method, the EC50 for the monomeric mRAPc peptide was measured as 20±1 nM (Table 4).

TABLE 4

|  | mRAPc | mRAPc + anti-biotin Ab | RAP |
| --- | --- | --- | --- |
| $EC_{50}$ (2 nM RAP d3) | 20 ± 1 | 3 ± 1 | 0.5 ± 5 |
| Maximum binding | 0.62 | 0.52 | 0.74 |
| $r^2$ | 0.99 | 0.99 | 0.89 |
| relative to monomer | 1× | 6.7× | 40× |

The combination of mRAPc with the anti-biotin antibody yielded an EC50 of 3±1 nM. Full-length RAP gave an EC50 of 0.5±5 nM. Antibody alone had no effect on the binding of RAP d3 to receptor. Preassembly of the antibody improved apparent mRAPc inhibitory potency more effectively than streptavidin, by about 7-fold. The EC50 for mRAPc in the presence of antibody remained 6-fold higher than that of full-length RAP. Therefore, as was the case with tetravalent streptavidin, addition of the bivalent antibody significantly improved the ability of the peptide to inhibit binding of RAP d3 to LRP1-C2.

The ability of multimerized mRAPc to inhibit binding of other LRP1-ligands was compared to inhibition by the mRAPc monomer and full-length RAP. Trypsin-activated α-2-macroglobulin and the uPA/PAI-1 complex were incubated in the presence of the mRAPc peptides at a single ligand concentration. In both cases, the complex of streptavidin and mRAPc inhibited binding with an EC50 approximately midway between RAP and the mRAPc monomer.

EXAMPLE 6

Evaluation of Entry into Liver of Cyclic RAP Peptide Oligomeric Combinations

In order to determine whether the multimeric peptide would replicate the in vivo bio-distribution behavior of full-length RAP following intravenous injection, the levels of mRAPc peptide accumulation in the liver were measured. Biotinylated RAP peptide, biotinylated RAP protein or buffer were combined with $^{35}$S-SLR-streptavidin (0.7 mCi/mL, 300 Ci/mmol, GE Healthcare) and dialyzed against phosphate-buffered saline (PBS) with D-TUBE™ dialysis cassettes (14 kD MWCO, EMD Biosciences). Male Sprague-Dawley rats (6-8 weeks) were injected with test materials (2 µL/g; ~20 µCi/rat) through a tail vein. Animals were sacrificed thirty minutes post-injection with pentobarbital (200 mg/kg). All subjects were treated in accordance with the guidelines set by the Canadian Council on Animal Care for the humane treatment of laboratory animals. Carcasses were frozen, embedded in carboxymethycellulose and sectioned for analysis by semi-quantitative whole-body autoradioluminography (QWBA) using a Fuji BAS-2500 phosphorimager. Clearly delineated areas within assayed organs for each animal were selected for luminescence analysis (Fuji Image Reader v1.1 and Fuji Image Gauge v3.12). Values are expressed in units of photostimulated luminescence per unit area ($PSL/mm^2$).

The preparation of $^{35}$S-labeled streptavidin was combined with the biotinylated mRAPc peptide, in a molar ratio of twenty to one, or with in vivo biotinylated RAP, in a molar ratio of five to one, and injected intravenously into rats. Labeled streptavidin alone was used as a control.

Streptavidin has been reported to accumulate in kidney, but not significantly in liver following intravenous injection (Wilbur, et al., Bioconjug Chem 9:100-107, 1998; Rosebrough, et al., J Nucl Med 37:1380-1384, 1996). In this experiment, the preparation of biotinylated RAP distributed to liver at levels 2.7-fold greater than that of streptavidin alone, and at similar or lower levels in all other tissues tested (FIG. 3). The mRAPc peptide, pre-assembled on labeled streptavidin, distributed to the liver at levels over 7-fold greater than that of streptavidin alone, and with similar or lower levels compared to control in all other tissues tested (FIG. 3). It is notable that high levels of competing LRP1 ligands in the blood were apparently unable to block liver uptake of the peptide complex, an observation made previously, for intravenously-administered full-length RAP (Warshawsky, et al., J Clin Invest 92:937-944, 1993).

In addition to the bio-distribution studies in the rat, distribution of mRAPc multimerized peptides were assessed in woodchucks, which are useful for studying liver disorders such as hepatocellular carcinoma (see Example 2). Bio-distribution studies were performed essentially as described above, using mRAPc-streptavidin and streptavidin alone as control. Results of the studies show that mRAPc-streptavidin uptake in the woodchuck liver (mean PSL/mm$^2$ of 1979) was approximately 4.5 fold greater than uptake of streptavidin alone (mean 435 PSL/mm$^2$).

These results show that multimerized mRAPc is efficiently taken up in vivo by the liver, and indicate that the multimerized RAPc will be an effective vehicle for administering therapeutic agents to the liver for the treatment of liver disorders.

Numerous modifications and variations in the invention as set forth in the above illustrative examples are expected to occur to those skilled in the art. Consequently only such limitations as appear in the appended claims should be placed on the invention

REFERENCES

1. Herz, J., Qiu, S. Q., Oesterle, A., DeSilva, H. V., Shafi, S., and Havel, R. J. (1995) Proc Natl Acad Sci USA 92, 4611-4615
2. Verges, M., Bensadoun, A., Herz, J., Belcher, J. D., and Havel, R. J. (2004) J Biol Chem 279, 9030-9036
3. Yu, K. C., Chen, W., and Cooper, A. D. (2001) J Clin Invest 107, 1387-1394
4. Bu, G., Maksymovitch, E. A., and Schwartz, A. L. (1993) J Biol Chem 268, 13002-13009
5. Narita, M., Bu, G., Olins, G. M., Higuchi, D. A., Herz, J., Broze, G. J., Jr., and Schwartz, A. L. (1995) J Biol Chem 270, 24800-24804
6. Li, Y., Lu, W., Marzolo, M. P., and Bu, G. (2001) J Biol Chem 276, 18000-18006
7. Marrero, J. A. (2006) Curr Opin Gastroenterol 22, 248-253
8. El-Serag, H. B., Mason, A. C., and Key, C. (2001) Hepatology 33, 62-65
9. El-Serag, H. B., and Mason, A. C. (2000) Arch Intern Med 160, 3227-3230
10. El-Serag, H. B., and Mason, A. C. (1999) N Engl J Med 340, 745-750
11. Zhu, A. X. (2006) Oncologist 11, 790-800
12. Gish, R. G. (2006) Clin Gastroenterol Hepatol 4, 252-261
13. Ribero, D., Abdalla, E. K., Thomas, M. B., and Vauthey, J. N. (2006) Expert Rev Anticancer Ther 6, 567-579
14. Lau, W. Y., Yu, S. C., Lai, E. C., and Leung, T. W. (2006) J Am Coll Surg 202, 155-168
15. Lin, X. D., and Lin, L. W. (2006) Hepatobiliary Pancreat Dis Int 5, 16-21
16. Chan, J. Y., Chu, A. C., and Fung, K. P. (2000) Life Sci 67, 2117-2124
17. Plosker, G. L., and Faulds, D. (1993) Drugs 45, 788-856
18. Iadonato, S. P., Bu, G., Maksymovitch, E. A., and Schwartz, A. L. (1993) Biochem J 296 (Pt 3), 867-875
19. Prince, W. S., McCormick, L. M., Wendt, D. J., Fitzpatrick, P. A., Schwartz, K. L., Aguilera, A. I., Koppaka, V., Christianson, T. M., Vellard, M. C., Pavloff, N., Lemontt, J. F., Qin, M., Starr, C. M., Bu, G., and Zankel, T. C. (2004) J Biol Chem 279, 35037-35046
20. Warshawsky, I., Bu, G., and Schwartz, A. L. (1993) J Clin Invest 92, 937-944
21. Davidsen, O., Christensen, E. I., and Gliemann, J. (1985) Biochim Biophys Acta 846, 85-92
22. Mahley, R. W., and Ji, Z. S. (1999) J Lipid Res 40, 1-16
23. Laithwaite, J. E., Benn, S. J., Marshall, W. S., FitzGerald, D. J., and LaMarre, J. (2001) Toxicon 39, 1283-1290
24. Hollestelle, M. J., Geertzen, H. G., Straatsburg, I. H., van Gulik, T. M., and van Mourik, J. A. (2004) Thromb Haemost 91, 267-275
25. Gao, Y. S., Chen, X. P., Li, K. Y., and Wu, Z. D. (2004) World J Gastroenterol 10, 3107-3111
26. Bu, G., and Schwartz, A. L. (1998) Trends Cell Biol 8, 272-276
27. Andersen, O. M., Schwarz, F. P., Eisenstein, E., Jacobsen, C., Moestrup, S. K., Etzerodt, M., and Thogersen, H. C. (2001) Biochemistry 40, 15408-15417
28. Lazic, A., Dolmer, K., Strickland, D. K., and Gettins, P. G. (2003) Biochemistry 42, 14913-14920
29. Fisher, C., Beglova, N., and Blacklow, S. C. (2006) Mol Cell 22, 277-283
30. Migliorini, M. M., Behre, E. H., Brew, S., Ingham, K. C., and Strickland, D. K. (2003) J Biol Chem 278, 17986-17992
31. Warshawsky, I., Bu, G., and Schwartz, A. L. (1993) J Biol Chem 268, 22046-22054
32. Melman, L., Cao, Z. F., Rennke, S., Marzolo, M. P., Wardell, M. R., and Bu, G. (2001) J Biol Chem 276, 29338-29346
33. Tennant, B. C., Toshkov, I. A., Peek, S. F., Jacob, J. R., Menne, S., Hornbuckle, W. E., Schinazi, R. D., Korba, B. E., Cote, P. J., and Gerin, J. L. (2004) Gastroenterology 127, S283-293
34. Danesi, R., Fogli, S., Gennari, A., Conte, P., and Del Tacca, M. (2002) *Clin Pharmacokinet* 41, 431-444
35. Hu, Y., Pang, E., Lai, P. B., Squire, J. A., MacGregor, P. F., Beheshti, B., Albert, M., Leung, T. W., and Wong, N. (2004) *Int J Oncol* 25, 1357-1364

TABLE 2

| d3 sequence | variable positions | | | | | | LRP2 CR89 | | LRP1 CR3-5 | |
|---|---|---|---|---|---|---|---|---|---|---|
| | 213 | 217 | 249 | 251 | 256 | 270 | $K_d$ (nM) | % max | $K_d$ (nM) | % max |
| RAP | S | E | H | E | K | K | NF | 5% | 16 ± 4 | 76% |
| RAP E217K | S | K | H | E | K | K | NF | 5% | 9 ± 1 | 91% |
| RAP H249Y | S | E | Y | E | K | K | NF | 2% | 28 ± 8 | 90% |
| RAP E251K | S | E | H | K | K | K | NF | 5% | 7 ± 1 | 100% |
| RAP K270E | S | E | H | E | K | E | NF | 2% | NF | 4% |
| RAP K256A, K270E | S | E | H | E | A | E | NF | 3% | NF | 2% |

TABLE 2-continued

| d3 sequence | variable positions | | | | | | LRP2 CR89 | | LRP1 CR3-5 | |
|---|---|---|---|---|---|---|---|---|---|---|
| | 213 | 217 | 249 | 251 | 256 | 270 | $K_d$ (nM) | % max | $K_d$ (nM) | % max |
| RAP E251K, K270E | S | E | H | K | K | E | NF | 2% | NF | 4% |
| RAP E251K, K256A, K270E | S | E | H | K | A | E | 114 ± 32 | 40% | NF | 2% |
| MegaRAP1 | T | K | Y | K | A | E | 38 ± 3 | 88% | NF | 4% |
| MegaRAP1 T213S | S | K | Y | K | A | E | 19 ± 1 | 94% | NF | 2% |
| MegaRAP1 K217E | T | E | Y | K | A | E | 25 ± 1 | 88% | NF | 2% |
| MegaRAP1 Y249H | T | K | H | K | A | E | NF | 35% | NF | 2% |
| MegaRAP1 K251E | T | K | Y | E | A | E | NF | 11% | NF | 2% |
| MegaRAP1 A256K | T | K | Y | K | K | E | NF | 2% | NF | 6% |
| MegaRAP1 E270K | T | K | Y | K | A | K | 8 ± 1 | 100% | 114 ± 31 | 85% |
| MegaRAP1 A256K, E270K | T | K | Y | K | K | K | 72 ± 11 | 73% | 4 ± 0.3 | 93% |
| MegaRAP1 K251E, E270K | T | K | Y | E | A | K | 153 ± 104 | 16% | NF | 16% |

What is claimed:

1. A method of delivering an active agent to the liver of a subject in need of an agent for treating a liver disorder comprising:

administering to said animal a conjugate comprising (a) a receptor binding moiety selected from the group consisting of Receptor Associated Protein of SEQ ID NO: 1 (RAP), a RAP fragment, and a RAP variant that retains RAP's binding affinity to LRP1 of about 1-5 nM, attached to (b) an active agent, wherein said RAP fragment or variant comprises an amino acid sequence at least 80% identical to SEQ ID NO: 4 and wherein said agent is delivered to the liver.

2. The method of claim 1 wherein the receptor binding moiety of said conjugate is a RAP fragment or variant missing at least 200 and up to 243 amino acids from the N-terminus of SEQ ID NO: 1.

3. The method of claim 1 wherein the receptor binding moiety of said conjugate is a RAP fragment missing at least 200 and up to 243 amino acids from the N-terminus of SEQ ID NO: 1.

4. The method of claim 2 or 3 wherein said RAP fragment or variant is missing 243 amino acids from the N-terminus of SEQ ID NO: 1.

5. The method of claim 2 or 3 wherein said RAP fragment or variant is further missing at least 4 and up to 11 amino acids from the C-terminus of SEQ ID NO: 1.

6. The method of claim 2 or 3 wherein said RAP fragment or variant is further missing 11 amino acids from the C-terminus of SEQ ID NO: 1.

7. The method of claim 1 wherein said RAP fragment or variant lacks amino acids 1-143 and 320-323 of mature RAP of SEQ ID NO: 1.

8. The method of claim 2 or 3 wherein said RAP fragment or variant comprises a continuous portion of RAP d3 (SEQ ID NO: 2) that is (a) at least 71 amino acids in length and (b) comprises amino acids 256-270.

9. The method of claim 1 wherein said receptor binding moiety is a cyclic RAP peptide that is less than 85 amino acids in length, comprising 50 contiguous amino acids that are at least 70% identical to SEQ ID NO: 4, and which binds to LRP1 with a Kd of about $1 \times 10^{-8}$ M or less.

10. The method of claim 1 wherein said receptor binding moiety is a RAP variant, said RAP variant comprising one or more conservative substitutions relative to native RAP of SEQ ID NO: 1.

11. The method of claim 1 wherein said receptor binding moiety is a RAP variant, said RAP variant comprising a mutation at any one of positions 217, 249, or 251 of mature RAP.

12. The method of claim 2 or 3 wherein said RAP variant comprises a mutation, wherein said mutation is the replacement of an acidic amino acid with a basic amino acid.

13. The method of claim 12 wherein said acidic amino acid is selected from the group consisting of D and E.

14. The method of claim 12, wherein said basic amino acid is selected from the group consisting of K and R.

15. The method of claim 2 or 3 wherein said RAP variant comprises a mutation, wherein said mutation is the replacement of a basic amino acid with an acidic amino acid.

16. The method of claim 15 wherein said basic amino acid is selected from the group consisting of K and R.

17. The method of claim 15, wherein said acidic amino acid is selected from the group consisting of D and E.

18. The method of claim 1 wherein said RAP variant comprises a mutation, wherein said mutation is the replacement of an amino acid selected from the group consisting of A, C, D, E, G, I, K, L, M, N, P, Q, R, S, T, and V with an amino acid selected from the group consisting of F, Y, W, and H.

19. The method of claim 1 wherein the receptor binding moiety of said conjugate is a RAP fragment or variant set out in SEQ ID NO: 9.

20. The method of claim 1, wherein the RAP, RAP fragment or RAP variant and diagnostic or therapeutic agent are linked through a linker.

21. The method of claim 20, wherein said linker is a peptide linker.

22. The method of claim 1 wherein the receptor binding moiety is an oligomeric combination of RAP fragments or RAP variants.

23. The method of claim 1 wherein the conjugate is in a pharmaceutical composition comprising a pharmaceutically acceptable carrier, diluent or excipient.

24. The method of claim 1 wherein the active agent is a cytotoxic agent.

25. The method of claim 24 wherein the cytotoxic agent is selected from the group consisting of Mechlorethamine hydrochloride, Cyclophosphamide, Ifosfamide, Chlorambucil, Melphalan, Busulfan, Thiotepa, Carmustine, Lomustine, Dacarbazine and Streptozocin.

26. The method of claim 1 wherein the active agent is a radioisotope.

27. The method of claim 26 wherein the radioisotope is selected from the group consisting of 131I, 125I, 111In, 90Y, 67Cu, 127Lu, 212Bi, 213Bi, 255Fm, 149Tb, 223Rd, 213Pb, 212Pb, 211At, 89Sr, 153Sm, 166Ho, 225Ac, 186Re, 67Ga, 68Ga and 99 mTc.

* * * * *